US012722022B1

United States Patent
John

(12) United States Patent
(10) Patent No.: US 12,722,022 B1
(45) Date of Patent: Sep. 1, 2026

(54) SYSTEMS AND METHODS FOR DUAL-PHASE TRANSCRANIAL STIMULATION

(71) Applicant: Michael Sasha John, Larchmont, NY (US)

(72) Inventor: Michael Sasha John, Larchmont, NY (US)

( * ) Notice: Subject to any disclaimer, the term of this patent is extended or adjusted under 35 U.S.C. 154(b) by 1207 days.

(21) Appl. No.: 17/450,594

(22) Filed: Oct. 12, 2021

Related U.S. Application Data

(60) Provisional application No. 63/235,776, filed on Aug. 22, 2021, provisional application No. 63/094,441, (Continued)

(51) Int. Cl.
*A61N 2/00* (2006.01)
*A61N 2/06* (2006.01)
*A61N 2/12* (2006.01)

(52) U.S. Cl.
CPC ............ *A61N 2/002* (2013.01); *A61N 2/006* (2013.01); *A61N 2/06* (2013.01); *A61N 2/004* (2013.01); *A61N 2/12* (2013.01)

(58) Field of Classification Search
CPC .......... A61N 2/002; A61N 2/006; A61N 2/06; A61N 2/36031
See application file for complete search history.

(56) References Cited

U.S. PATENT DOCUMENTS 6,425,852 B1 * 7/2002 Epstein .................. A61N 2/006 600/15
9,962,555 B1 * 5/2018 Charles .................... A61N 2/06
(Continued)

FOREIGN PATENT DOCUMENTS

WO WO-2015079319 A1 * 6/2015 ........... A61N 1/0456
WO WO-2019143790 A1 * 7/2019 ........... A61B 5/4836
(Continued)

OTHER PUBLICATIONS

Chaffee et al "A Method for the Remote Control of Electrical Stimulation of the Nervous System" Dec. 1934, vol. 7 (Issue 2) pp. 83-128; The Yale Journal of Biology and Medicine (Year: 1934).*
(Continued)

*Primary Examiner* — Christine H Matthews
*Assistant Examiner* — Brooke Nicole Kohutka
(74) *Attorney, Agent, or Firm* — Rosenberg, Klein & Lee

(57) ABSTRACT

Systems and methods improving patient benefit from stimulation therapy including transcranial magnetic stimulation (TMS) are disclosed. Treatment may include a first and second type of stimulation treatment provided as simultaneous, interleaved, or sequential stimulation. Treatment sequence and treatment session characteristics for the first or second stimulation type may be set or adjusted based on a patient's characteristics or response to stimulation meeting a minimum selected criterion. Combination therapy with at least two therapy types may obviate the need for repeated clinic visits which use TMS devices and protocols with stronger fields or other technical requirements. Stimulation targeting at least one cranial nerve with magnetic stimulation is also disclosed.

23 Claims, 8 Drawing Sheets

Related U.S. Application Data filed on Oct. 21, 2020, provisional application No. 63/090,240, filed on Oct. 11, 2020.

(56) References Cited

U.S. PATENT DOCUMENTS

| | | | | |
|---|---|---|---|---|
| 11,253,718 | B2 * | 2/2022 | Prouza | A61N 2/008 |
| 2010/0185042 | A1 * | 7/2010 | Schneider | A61N 2/004 600/13 |
| 2014/0235929 | A1 * | 8/2014 | Rohan | A61N 2/006 600/14 |
| 2015/0148878 | A1 * | 5/2015 | Yoo | A61N 1/0456 607/148 |
| 2017/0106201 | A1 * | 4/2017 | Schwarz | A61N 5/0625 |
| 2017/0246481 | A1 * | 8/2017 | Mishelevich | A61N 2/008 |
| 2019/0126039 | A1 * | 5/2019 | Yoo | A61N 1/36007 |
| 2019/0201707 | A1 * | 7/2019 | Stubbeman | A61N 2/004 |
| 2021/0196971 | A1 * | 7/2021 | Lowin | A61N 2/12 |

FOREIGN PATENT DOCUMENTS

| | | | | |
|---|---|---|---|---|
| WO | WO-2021026415 | A1 * | 2/2021 | A61N 2/06 |
| WO | WO-2022016106 | A1 * | 1/2022 | A61N 2/02 |

OTHER PUBLICATIONS

Peterson et al "Evidence Brief: Factors that Optimize Therapy with Repetitive Transcranial Magnetic Stimulation for Treatment-Resistant Depression" Sep. 2014, pp. 1-42; Department of Veterans Affairs Health Services Research and Development Service-Evidence-based Synthesis Program (Year: 2014).*

Bourla et al "Variability in Motor Threshold during Transcranial Magnetic Stimulation Treatment for Depression: Neurophysiological Implications" Aug. 26, 2023, 13(9):1246; Brain Sci. (Year: 2023).*

Dolberg et al "Magnetic motor threshold and response to TMS in major depressive disorder" Mar. 25, 2002, 106: pp. 220-223; Acta Psychiatr (Year: 2002).*

* cited by examiner

SYSTEMS AND METHODS FOR DUAL-PHASE TRANSCRANIAL STIMULATION

REFERENCE TO RELATED APPLICATIONS

This Patent Application is based upon U.S. Provisional Pat. App. Ser. No. 63/090,240 filed Oct. 11, 2020, U.S. Provisional Pat. App. Ser. No. 63/094,441 filed Oct. 21, 2020 and U.S. Provisional Pat. App. Ser. No. 63/235,776 filed Aug. 22, 2021.

INCORPORATION BY REFERENCE

This Patent application hereby incorporates by reference, U.S. Patent Applications Ser. Nos. No. 63/090,240, 63/094,441, 63/235,776 which are hereby incorporated by reference in entirety for all purposes.

FIELD

This invention is in the field of modulating biological tissue and especially with respect to modulating brain, cranial nerve, or spinal tissue.

BACKGROUND

A large variety transcranial stimulation systems exist for providing therapy using energy such as electrical or magnetic stimulation. Transcranial magnetic stimulation (TMS) including repetitive TMS (rTMS) systems are typically large, heavy, and expensive and are designed for use in a clinical setting where a patient undergoes a therapy session conducted by a doctor or suitably trained technician. The generation of strong magnetic fields may require liquid cooling of the device. TMS treatment can typically include daily (weekday) sessions where stimulation treatment is provided using a strength determined to be at or above motor threshold for an interval of between 20 to 60 minutes, and often for about 30-40 minutes. A course of treatment may occur 5-days a week across a treatment interval of approximately 4 to 7 weeks.

Although, rTMS has emerged as a safe, effective treatment for patients having various disorders there is a need for improved TMS therapy. For example, while some medication-resistant depression patients may experience a therapeutic response with symptom improvement for a year or longer, this may be limited to 6 months (or less) for as many as 40% of responders (e.g., Dunner D L, Aaronson S T, Sackeim H A, et al. *A multisite, naturalistic, observational study of transcranial magnetic stimulation for patients with pharmacoresistant major depressive disorder: Durability of benefit over a* 1-*year follow-up period*. J Clin Psychiatry. 2014; 75(12):1394-1401). To be considered an appropriate candidate for treatment of depression with TMS, the patient should, at a minimum, have a confirmed diagnosis by a psychiatrist of severe major depressive disorder (single or recurrent episode), documented by standardized rating scales that reliably measure depressive symptoms (e.g., Beck Depression Scale [BDI], Hamilton Depression Rating Scale [HDRS], Montgomery-Asberg Depression Rating Scale [MADRS], etc.) and have failed antidepressant treatment by medication. Treatment programs that are reimbursed by payors may consist of a maximum of 30 sessions (e.g., 5 days a week for 4-6 weeks) plus 4-6 tapering sessions where TMS occurs less frequently (e.g., 6 sessions over three weeks). Treatments beyond 36 sessions (e.g., 30 treatment sessions followed by 6 tapering sessions) may be reviewed for medical necessity if the patient met a minimum improvement criterion to the prior course of TMS therapy. Tapering sessions may are a limited schedule of less frequent therapy that occurs after an initial course of treatment having a more frequent schedule of stimulation. Although TMS may also provide therapy for other disorders and conditions such as post-traumatic stress disorder (PTSD), obsessive-compulsive disorder (OCD), anxiety or addiction disorders, the accepted treatment protocols are not yet widely established.

The literature does not provide well-established, accepted, and evidenced-based support or guidelines for treatment schedules and protocols that may best result in and then maintain a therapeutic benefit for those that may (otherwise) experience lack of treatment response or relapsing symptoms. It is not yet known if treatment longer than 4-6 weeks may improve response rates, amount of therapy benefit, or how consistently tapering rTMS sessions benefit individual patients, or how frequently follow-up treatment sessions should be scheduled to be effective.

If depression improves with initial rTMS, and then a patient's symptoms return at a later period, then an rTMS course of treatment can be repeated (with a similar or less frequent treatment schedule). Repeating the treatment on a patient after a full treatment cycle of TMS has been provided to a patient is sometimes termed "re-induction" or "booster therapy", which may be covered by some insurance. Treatment with TMS which occurs after 4-6 week period of weekday therapy may be referred to using many terms: extended taper, rescue stimulation, booster sessions, re-introduction, refresher, re-treatment, etc.

rTMS systems and accessories which are intended to be used in the clinic to provide stimulation at, or above motor threshold have been commercialized by companies such as Magstim, MagVentures, Wave Neuroscience, CloudTMS, NexStim, Neuronetics, and Brainsway. Systems developed for at-home use have been developed by eNeura (using a limited set of pulses for migraine treatment) and NeoSync (for providing subthreshold TMS stimulation for various indications including depression), marketed by Wave Neuroscience. eNeura uses a conventional magnetic coil to provide a portable TMS device. Magnetic stimulation may be brief and provide only 1 or several pulses per day in response to onset of migraine.

The NeoSync device uses a system of neodymium cylindrical magnets that rotate to provide stimulation at a selected frequency. This can be matched to a peak frequency of patient's electroencephalogram (EEG) such as peak posterior alpha. An alternative system has more recently been developed that also provides similar lower strength stimulation and is termed a transcranial, rotating, permanent magnet stimulator, or "TRPMS". The TRPMS can be realized as a non-invasive, portable, multifocal neuromodulator configured to (simultaneously) modulate multiple cortical regions to, for example, enhance or attenuate strengths of functional connections between these regions. This therapy is being investigated for therapies related to, for example, stroke recovery. It is posited that weak or low intensity transcranial stimulation of the brain, such as low field magnetic stimulation and electrical stimulation, can produce significant functional and therapeutic neuromodulatory effects. (Helekar, S. et al. (2018). The strength and spread of the electric field induced by transcranial rotating permanent magnet stimulation in comparison with conventional transcranial magnetic stimulation. Journal of Neuroscience Methods, 309, 153-160).

A miniaturized rTMS device (Brain Stim; REMED), has been designed which contains a figure-of-eight, 80-mm diameter wearable rTMS coil connected to a downsized stimulator and which was shown to provide clinical benefit using subthreshold stimulation (e.g Lee S, Jang K I, Yoon S, Chae J H. The Efficacy of Miniaturized Repetitive Transcranial Magnetic Stimulation in Patients with Depression. Clin Psychopharmacol Neurosci. 2019; 17(3):409-414). The wearable TMS coil can provide 0.5 to 2.5 tesla stimulation at up to 100 Hz using a biphasic waveform with a pulse width of about 320 ms. While results of different studies have suggested that suprathreshold rTMS stimulation results in better treatment response than subthreshold rTMS for treatment of psychiatric disorders (e.g., depression), subthreshold stimulation may still provide treatment benefit, at least in some patients. Subthreshold rTMS may inhibit cortical/corticospinal excitability and may permit neural facilitation and post-tetanic potentiation.

Other technologies that can be used to stimulate the brain are transcranial electrical stimulation therapies which use transcranial direct current stimulation (tDCS) and alternating current stimulation (tACS). tDCS can be realized as portable, wearable brain stimulators that deliver a low electric current to the scalp. A fixed current between 1 and 2 mA is typically applied. tDCS works by applying a positive (anodal) or negative (cathodal) current via electrodes to one or more areas of the scalp. Systems that use multiple sets of electrodes are available that can provide customized and spatially detailed programs of stimulation (e.g., www.soterixmedical.com). Studies support these technologies can be used in the treatment of various disorders such as major depressive disorder (MDD; e.g., Bennabi, D., & Haffen, E. (2018). *Transcranial Direct Current Stimulation* (*tDCS*): *A Promising Treatment for Major Depressive Disorder? Brain sciences,* 8(5), 81). Brain activity can also be modulated using ultrasound stimuli or other types of energy. For example, Pulsed Electromagnetic Field Treatment "PEFT" can be used (which may also be referred to as Pulsed Electromagnetic Fields "PEMF", Pulsed electromagnetic energy "PEME", Pulsed Shortwave Therapy "PSWT"). These types of stimulation devices may be incorporated into embodiments of the disclosed invention.

Existing treatments using magnetic or electrical stimulation have shown promise for providing brain treatment to treat or at least improve symptoms related to, for example, psychiatric disorders such as depression, OCD, and anxiety, addictive behaviors, stroke, cognitive disorders, and disorders such as pain. However, new treatment systems and methods are needed to provide advantages including, for example, improving overall therapy benefit, reducing the delay before benefit occurs, reducing the number of patients who are refractory to, or who relapse after receiving currently approved therapies.

SUMMARY OF THE INVENTION

In embodiments, an object of the invention is to provide multi-phase treatment, which may be realized using a dual-phase treatment embodiment, but which may have additional treatment phases including "Booster" treatment sessions, to provide therapy that is sufficient to provide clinical benefit or which provides improved benefit over that obtained using only one phase of treatment.

In embodiments, an object of the invention is to provide dual phase (or multi-phase if more than 2 phases are used) treatment to improve chance of clinical benefit over that obtained either of its constituent therapies by including, for example, a) intervals of stronger stimulation, typically missing from therapies provided by lower strength stimulation devices, or b) inter-session booster or maintenance treatments to supplement stronger (e.g., supra-threshold) stimulation procedures typically accomplished under medical supervision in a doctor's office.

In embodiments, an object of the invention is to provide a method including providing a combination of suprathreshold stimulation (e.g., above a defined threshold such as a subject's motor threshold "MT") and subthreshold stimulation during different time intervals.

In embodiments, an object of the invention is to provide a method that includes providing a combination of suprathreshold induction stimulation and subthreshold stimulation maintenance.

In embodiments, an object of the invention is to provide a method that includes providing a combination of suprathreshold induction stimulation and subthreshold stimulation maintenance and suprathreshold booster stimulation.

In embodiments, an object of the invention is to provide a method including providing a combination of suprathreshold stimulation in combination with subthreshold stimulation.

In embodiments, an object of the invention is to provide methods includes providing a stimulation that targets at least one cranial nerve. The cranial nerves are a portion of the peripheral nervous system that are routed directly from the brain rather than through the spinal cord and include 12 nerves in addition to the terminal nerve. In embodiments, TMS may be directed at one or more cranial nerves on the top of the head or the face, and may be provided laterally or bilaterally.

In embodiments, an object of the invention is to provide a method that includes providing a stimulation that targets at least two cranial nerves.

In embodiments, an object of the invention is to provide a method including providing either subthreshold or suprathreshold stimulation that is sufficient to produce a change in a measure that confirms the stimulation is making a change in a patient that is above a confirmatory threshold such as a change in a cardiac measure (e.g., heart rate, heart rate variability), or a sympathetic or parasympathetic measure, or biometric measures such as eye movement or pupil dilation measures (e.g., revisits, average fixation duration, or heatmap profile of position).

In embodiments, an object of the invention is to provide a method of providing stimulation using at least two different magnetic stimulation signals that target at least two cranial nerves, to modulate activity of two different target brain regions.

In embodiments, an object of the invention is to provide a system including both an electrical stimulator and magnetic stimulator under control of at least one processor operating according to a therapy protocol defining stimulation parameters and/or schedules that are configured to provide combination therapy to a patient.

In embodiments, an object of the invention is to provide multi-phase treatment that selects or adjusts the treatment protocols (dates and durations, stimulation strengths, intertherapy intervals, stimulator locations/regions to be stimulated, and other characteristics of two or more treatment protocols) that are defined in a "treatment series". Further the adjustment can occur according to a treatment criterion such as a detecting a minimum improvement, a minimum change in a subjective measure such as obtained using a quality-of-life (QOL) scale, a minimum change in an objective measure such as a neuroimaging value (e.g., quantitative EEG (QEEG) value or a brain network modeled value).

In embodiments, an object of the invention is to provide a treatment series that is adjusted according to parameters such as: the severity of the disorders; the response to an interval of treatment; results of an assessment battery; parameters of a brain network modelled from structural and/or functional imaging data; structural imaging data related to the shape or thickness of a patient's skull or the position of target tissue below the patient's skin; results of QOL instruments which are used to survey a patient at one or more times (e.g., change in the QOL; and/or, other measures.

In embodiments, an object of the invention is to provide a hybrid treatment series that combines at least 2 therapy devices, phases of sequential or interleaved therapy, intensity levels of stimulation, therapy protocols, or types of therapy to provide improved therapy.

In embodiments, an object of the invention is to provide therapy systems and methods that allow more sustained treatment response after an initial "induction" course of treatment, or which serve to supplement conventional TMS treatments which use supra-threshold stimulation to improve clinical response, increase the interval across which benefit is obtained and decrease rate of symptom relapse.

In embodiments, features of systems and methods disclosed herein can be used with only one type of device or treatment protocol using one type of therapy.

These and other objects and advantages of the invention will now be further disclosed.

DETAILED DESCRIPTION OF THE INVENTION

Therapy Protocols

Figure 1:
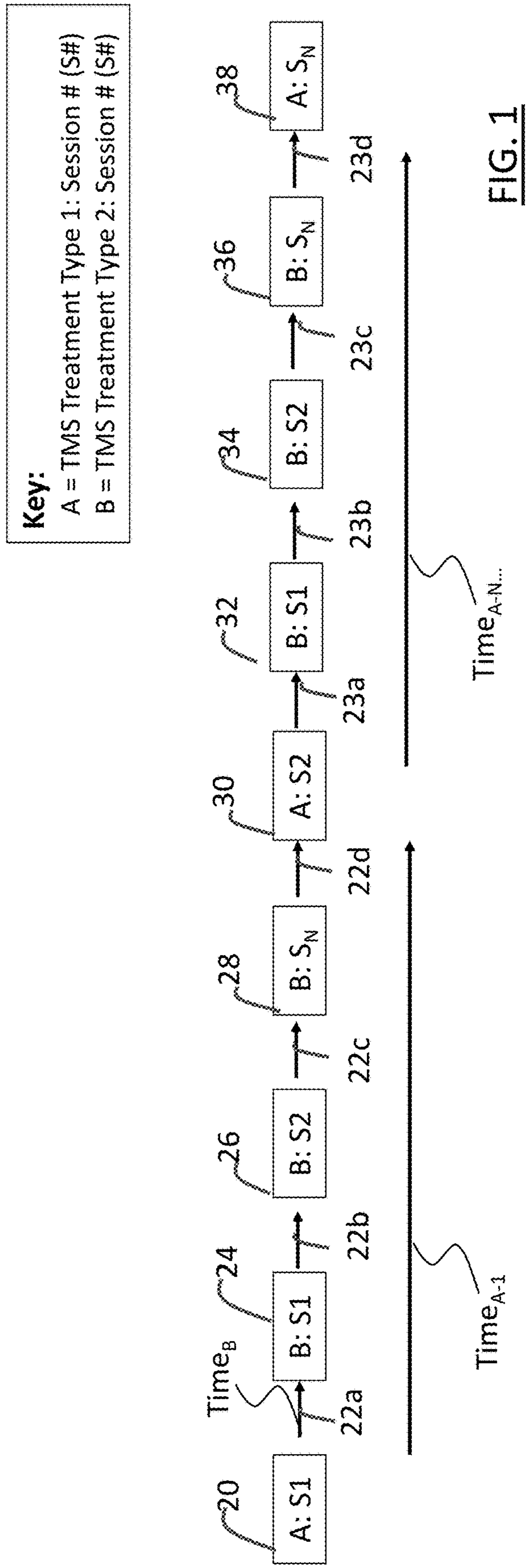
FIG. 1 is a diagrammatic representation of a combination treatment having a protocol with treatments of Type 1 and Type2.

In embodiments, in contrast to conventional TMS therapies that treat subjects for a selected interval with a single type of protocol when treating a disorder such as depression, the systems and methods of the invention disclose less discrete therapy regimens. FIG. 1 shows an embodiment of the invention which is combination therapy treatment protocol including two treatments types labeled as "A" or "B".

Figure 4:
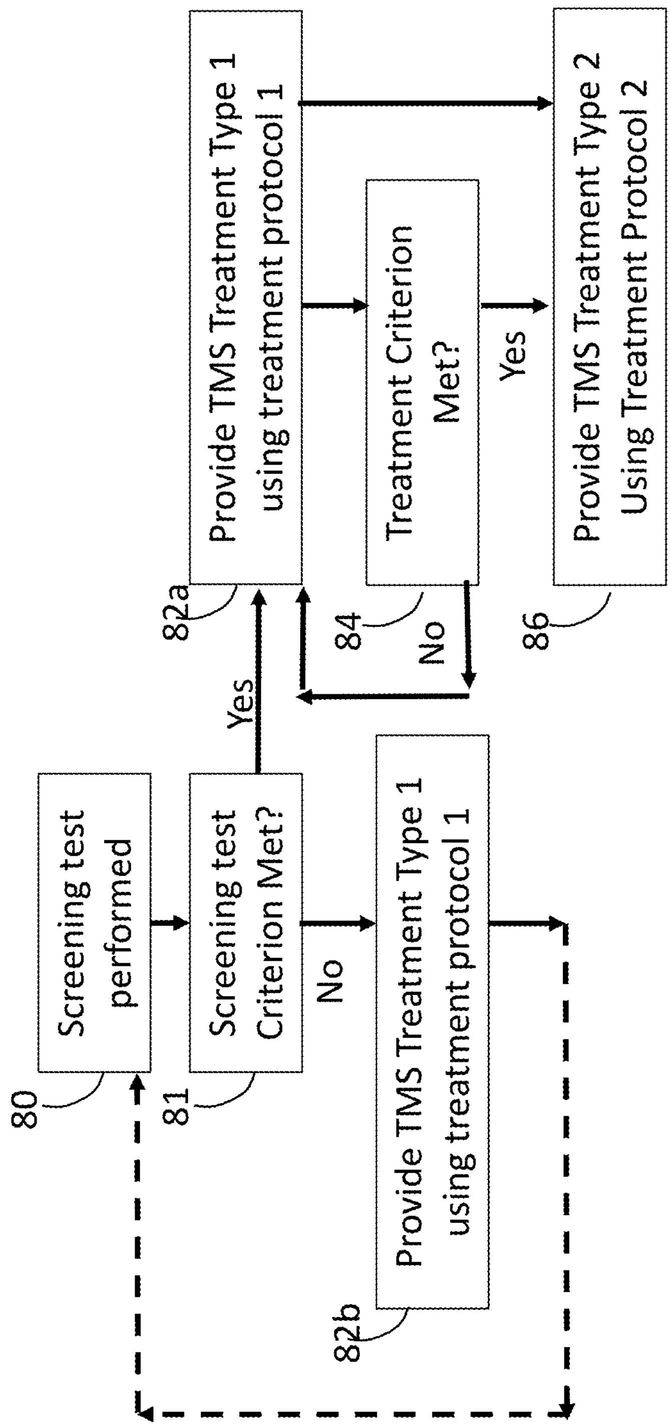
FIG. 4 shows a method of contingently adjusting a treatment protocol based upon criteria.
Figure 5B:
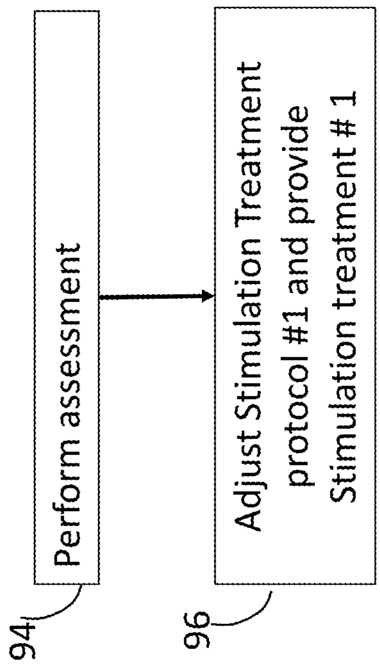
FIGS. 5*a*-5*c* show further alternative methods of contingently adjusting treatment protocols based upon assessment and criteria.
Figure 5A:
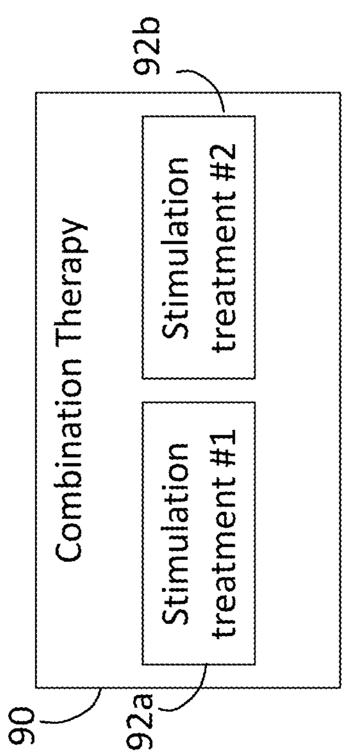
Figure 5C:
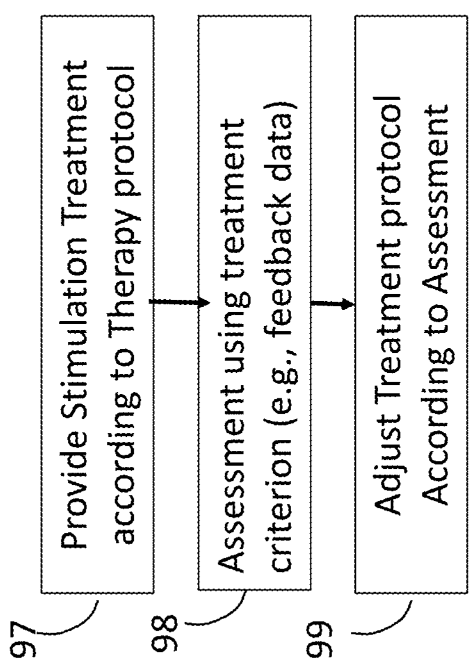
Figure 6:
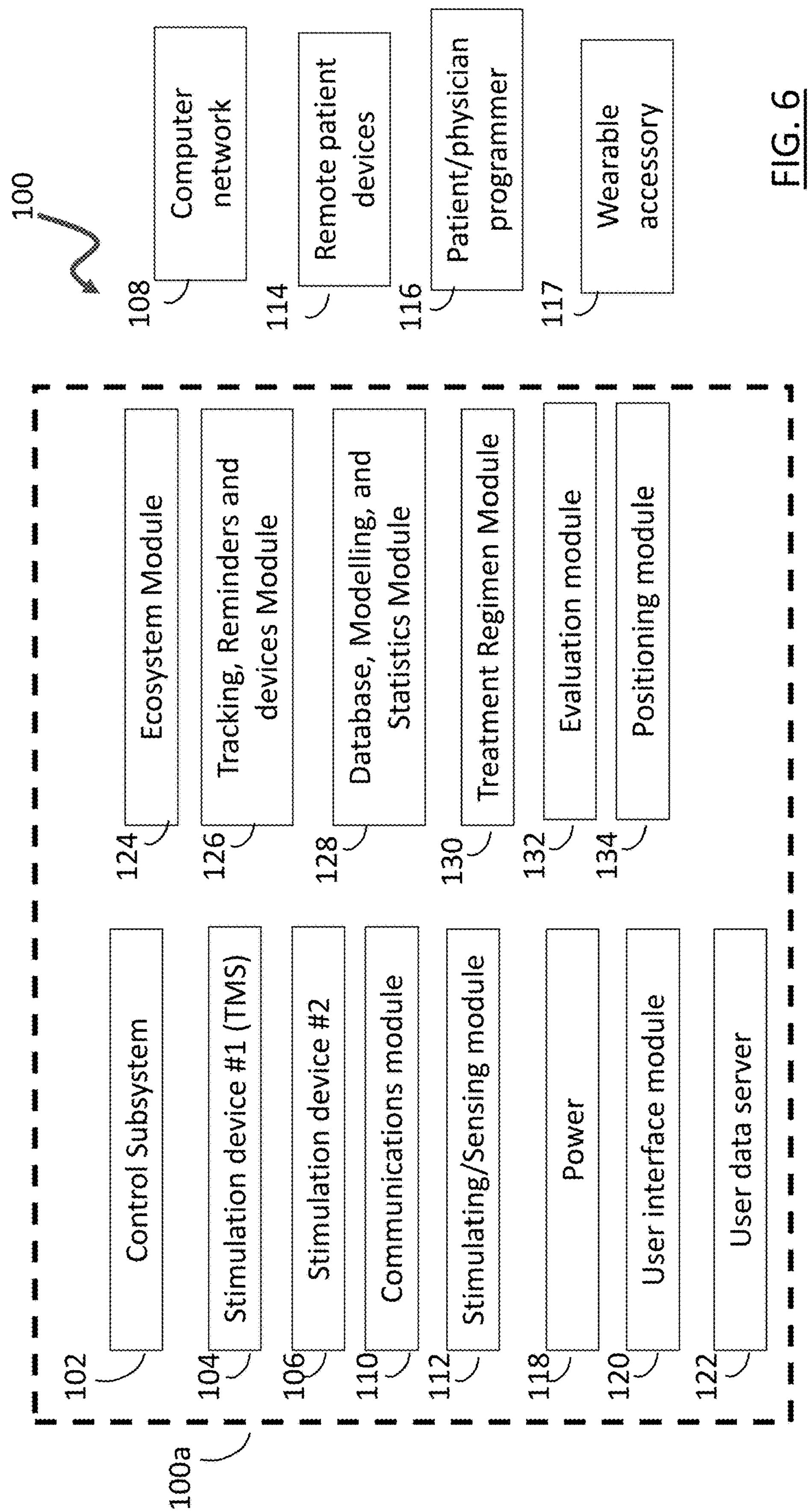
FIG. 6 shows an illustrative embodiment of a transcranial stimulation system.

In embodiments, the combination treatment is realized as a treatment protocol provided as steps of a treatment method such as shown in FIGS. 3-5*c*, or is provided as a treatment series defined as parameter values of a treatment program of a control subsystem module 102 that controls at least one stimulation device 104, 106 as seen in the system 100 of FIG. 6. The treatment program of FIGS. 1 and 2 can be defined in computer software or hardware memory of the system 100.

In an embodiment, a first type of TMS treatment designated "Type 1" or "A" is provided using a first treatment protocol as part of a first treatment session 20. The first treatment session may have protocol parameters that define at least a 20-30 minutes duration of TMS of treatment. After the first treatment 20 occurs using the first TMS treatment protocol, the patient may then be provided with treatment using the second TMS treatment protocol for up to N-treatment sessions (B:S1, B:S2 . . . B:$S_N$), before a second treatment with the first protocol 30 is provided (A:S2). This is followed by a series of treatments using the second treatment type (32, 34, 36) before the first type of treatment 38 is then again provided (A:$S_N$). In embodiments, this series of interleaved treatments serves as an induction protocol that provides a combination of two types of complimentary stimulation types to increase the total brain stimulation over that which would otherwise typically occur with only type 1 treatment (e.g., clinic based supra-threshold TMS treatment). Alternatively, this combination therapy protocol defines a dual-phase maintenance therapy in which TMS booster sessions at supra-threshold levels are supplemented by lower intensity subthreshold stimulation.

In an embodiment, a treatment regimen protocol defines the characteristics of each stimulation session of the Type 1 and Type 2 treatment sequences. Each treatment sequence defines protocol parameters such as the durations, inter-stimulation time intervals 22*a*-22*d*, 23*a*-23*d*, stimulation strength, frequency, stimulator type, and location(s) of TMS provided by one or more stimulators. The times that are defined to elapse between Type B treatments (TimeB, e.g., 22*b*, 22*c*, 23*b*, 23*c*), and the times between Type A treatments (TimeA-1) are defined as part of the treatment protocol associated with the treatment sequence. In an alternative embodiment, the treatment sequence protocols for either Type 1 or Type 2 therapy are adjusted dynamically based upon patient response to the treatment which can be assessed (e.g., assessed in relation to at least one treatment criterion as per FIG. 5*c*) using at least one of changes in objective measures, changes in subjective measures, or both. The assessment can use a set of surveys related to the QOL or symptoms severity for a selected disorder.

In embodiments, one or more of the treatment sessions (20-38) may include conducting an assessment of the patient before, during, and/or after the treatment is provided. The assessment battery of measures may include having the patient complete paper or electronic surveys or instruments such as health related quality of life (HRQOL) instruments related to assessment of QOL or patient symptoms related to, for example depression, anxiety, and the like. The scores derived from these instruments (or the difference in the current score and a prior baseline score) can be assessed and compared to treatment criteria to contingently set or adjust aspects of the treatment series protocol such as the timing between treatment sessions, treatment protocol parameters such as strength, timing, pulse width or rate of stimulation used by TMS transducers (e.g., Hz), duration of a treatment session, locations of stimulation, inter-session interval value etc.

In embodiments, the induction inter-session interval (Time A-1) is set to a value such as preferably 1-3 days, or 3-7 days according to a treatment schedule of the treatment regimen. Time A-N is a set interval or can be adjusted to be shorter or longer than Time A-1 as treatment progresses. Time A-N can be set depending upon patient response to the treatment after a selected time interval or number of treatments of the series. In other words, the interval defined by TimeA-N can be adjusted contingently based upon the patient showing (and/or maintaining) sufficient improvement in at least one measure of the assessment battery, where the sufficient level is defined in relation to meeting at least one treatment criterion of a set of treatment criteria (e.g, as per FIG. 5*c*).

For example, the inter-session delay value for TMS Type A therapy (Time A-1) can be initially set at preferably 1 to 3 days, or 3-7 days, but this can be iteratively increased to a maximum value such as about 7 or 15 or 30 or 45 or 60 or 90 or 120 days. The interval can be increased in as series of steps as long as assessment of the patient meets a therapy criterion indicating that the dual-phase therapy treatment continues to provide at least a minimum desired benefit to a patient. If the treatment series does not continue to provide sufficient benefit then the length of time between sessions of Type 1 or Type2 can be decreased, or iteratively decreased, as a series of steps each lasting a defined interval. Further, booster treatment sessions, or booster treatment session clusters, can be provided to re-establish therapy benefit.

In embodiments, the Times interval between sequential treatments using Type 2 treatment can be shortened or the treatment session can be lengthened if the patient does not show benefit. For example, while the treatment series protocol may initially set treatment duration at 30 minutes per day, this is increased so treatment occurs twice a day or for 60 or 120 minutes each day.

In embodiments, Type A therapy is suprathreshold TMS which is defined to meet a selected suprathreshold criterion such as the ability to induce an action potential or other objective measure in the patient (or has been shown to do this on a group of patients) inducing a noticeable sensation, or being above motor threshold (>MT), and Type B Therapy is subthreshold (i.e. does not meet this criterion) stimulation provided by TMS, tDCS, or tACS device that is configured to stimulate the brain, at least one cranial nerve, spinal cord, or a combination. Stimulation of a cranial nerve or spinal cord target may be more effective since these targets may be closer to the stimulator than brain tissue.

Not to be limited by theory, it may be challenging to detect a statistically significant or medically meaningful clinical improvement when using weaker TMS systems in isolation because the elicited clinical response is not as large as that seen with stronger magnetic stimulation. In embodiments, a low-strength TMS device (e.g., the NeoSync EEG Synchronized TMS device or "NEST") can be used to supplement a first type of TMS therapy that is provided in office using high-strength magnetic stimulation fields that meet a threshold criterion such as being above motor threshold. This dual phase therapy can provide better therapy outcomes compared to that which would be obtained using either therapy alone. An advantage provided by this combination treatment strategy is that the weaker therapy reinforces, supplements, and maintains the therapy benefit provided by the suprathreshold TMS therapy. Stimulation with lower level stimulation may also increase the capacity or responsiveness of the brain to higher intensity stimulation by mechanisms such as priming when this is provided within a window the precedes the higher level stimulation such as between 2 and 12 hours prior.

Figure 2:
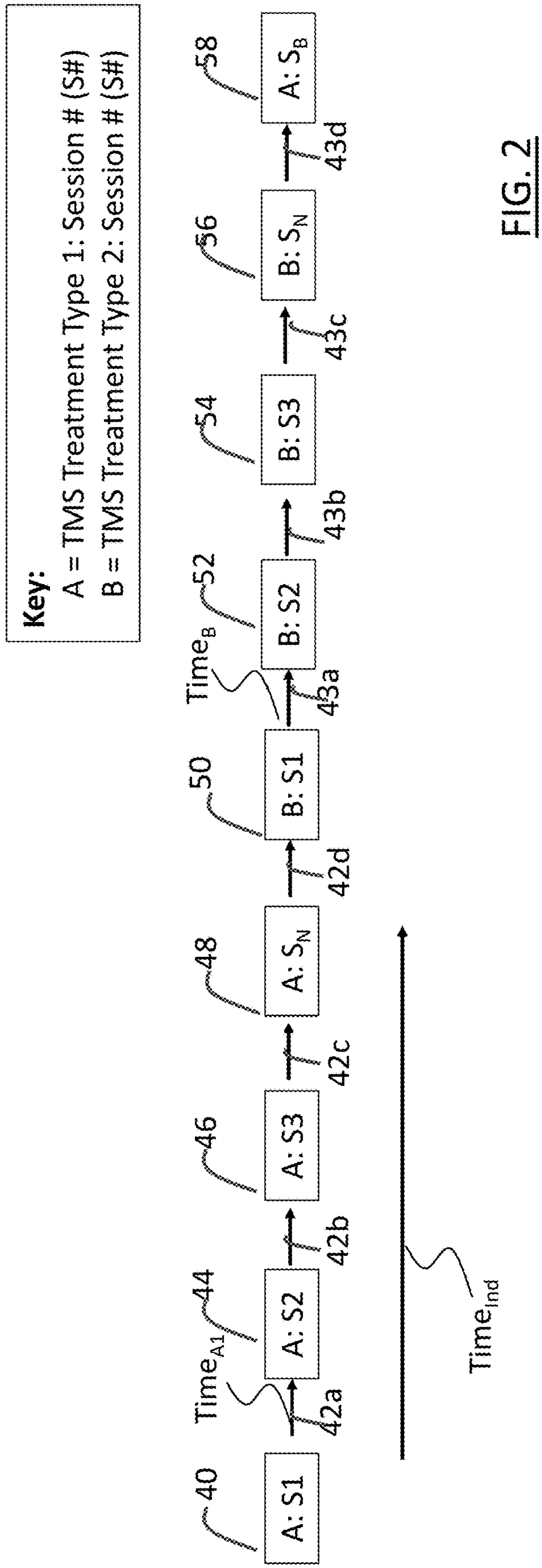
FIG. 2 shows a flow diagram of an alternative combination treatment having treatments of Type 1 and Type 2.

FIG. 2 shows an alternative embodiment of a combination treatment protocol including Type 1 and Type 2 treatments, where a first type of TMS treatments (e.g., 40-48) are provided according to a schedule defined for induction interval ($Time_{ind}$) and a second type of TMS treatments are provided thereafter for a defined maintenance schedule (52, 54, 56). The first stimulation treatment session 40 provides the first TMS treatment type. In embodiments this lasts, for example, 20-60 or 30 to 45 minutes. After a time interval 42*a* elapses, such as 1 or 2 days, a second treatment session occurs according to an induction protocol. The characteristics of the stimulation treatment such as the number of treatment sessions (e.g., 40, 44, 46, 48), intervals between treatment sessions of the same treatment type (42*a*, 42*b*, 42*c* and 43*a*, 43*b*, 43*c*) or intervals between different treatment types (42*d*, 43*d*), or total interval during which the treatment sessions occur during the induction phase of the treatment (Time Ind) can be set or these values may be contingently adjusted based upon such factors as: symptom severity; a patient showing an absolute or relative improvement in a measure; or, a change in a measurement that surpasses a treatment criterion. The induction series of treatments may be defined or continued until at least one of the following occurs: a selected number of treatment sessions have occurred (SN), a predefined total or a minimum number of treatments are provided, a positive treatment response is detected for, or reported by, the patient (e.g., as assessed in relation to a treatment criterion of step 98 of FIG. 5C).

In embodiments, the induction interval (Time A-Ind) is set to a value such as between 3 and 6 or 7 and 12 weeks, or between 6 and 9 weeks, or alternatively the length of the induction interval (and total number of sessions "SN") can be adjusted contingently based upon a patient profile, symptom severity, or the patient showing sufficient improvement in at least one measure of the assessment battery, where sufficient is defined in relation to meeting at least one criterion of a set of treatment criteria (e.g. see steps 94 and 98 of FIGS. 5*b* and 5*c*).

In an embodiment, a low-strength TMS device that provides subthreshold stimulation is used after a series of treatments using a first therapy that uses a high-strength TMS device that provides suprathreshold stimulation during an induction period. The induction period is initially used to elicit a therapeutic response in the patient that exceeds a selected treatment threshold. After an assessment step (as can be provided between step 48 and 50) indicates the treatment threshold is exceeded, the second type of therapy is then used to maintain benefit-if this does not occur then the interval during which induction occurs (Time-ind) can be extended. Alternatively, the transition simply occurs when the induction period is completed. Accordingly, the subthreshold stimulation is used to maintain rather than to induce the initial clinical response to TMS. Further, the second type therapy may periodically be supplemented by the provision of "Booster Therapy" 58 which includes one or more treatment sessions using the high-strength TMS device, suprathreshold stimulation, and associated stimulation protocol.

In embodiments, the combination dual-phase TMS therapy is used only for patients who have passed a screening test criterion (e.g., 59 of FIG. 3) which may be provided prior to and/or after a first treatment session 40 and indicates the patient may be an appropriate candidate for combination treatment with low-strength TMS. Meeting this criterion may include, for example, showing an MT response at a lower stimulation strength range. Many factors may contribute to enabling lower-strength stimulation to produce benefit in certain individuals. Another screen test criterion can be showing a biometric change to lower-strength stimulation that may be below, but close to MT. Additionally, the screening test may include using neuroimaging data (e.g., MRI data, x-ray; computerized tomography (CT) or computerized axial tomography (CAT) scan image data) to calculate the strength of the field at the brain after accounting for attenuation due to patient characteristics such as skull thickness, distance from TMS transducer to target brain region, and/or difference in brain structural or functional anatomy. Screening test criteria can improve the chance that the low-strength TMS treatment (e.g., the stimulation protocol settings) is able to provide clinical benefit and/or generate pulses of sufficient strength/duration to adequately stimulate the brain, cranial nerve, spinal cord, or other anatomical target. Screening criteria may include confirming the skull thickness or stimulator-brain distance is below a selected amount. Screening criteria may include requiring a subject to demonstrate a minimum defined change in cardiac or other biometric measure in response to stimulation of a selected strength (e.g., change in heart rate or heart rate variability). The response to the stimulation may be assessed in a time locked or non-time locked manner with respect to the timing of one or more stimulation pulses or bursts.

The screening test can be provided using pulses at a sufficiently low strength, using a coil or other transducer, that allows assessment of the subject to determine if the screening criterion is met. Screening criteria may include showing a minimum sensitivity to TMS as evidenced by a minimum change in EEG/QEEG measures, or which includes a minimum change that occurs within a selected time window after TMS, the change being associated with increased sensitivity to TMS (e.g., the size of the post-stimulation change in EEG relative to a baseline, or the rate at which the change decreases over time after the stimulation is provided).

In embodiments, the screening criterion may be defined as a showing a that minimum threshold level of stimulation produces a change in the patient (e.g., an MT threshold level is below a selected strength that is defined in relation to the TMS protocol that is used in the maintenance part of the therapy). In other words, a TMS coil can be set to provide a stimulation signal that is the same as, or set in relation to, that which will be provided by a weaker TMS device during the second type of therapy. This assessment is done to determine if there is a change at approximately that lower-strength stimulation level (e.g., lower peak intensity level, pulse duration, or both) that will be used outside of the clinic during supplemental or maintenance treatment. Alternatively, the stimulation is presented at 2 or more stimulation strengths. Stimulation evoked measures are made at both strengths and are used to calculate a slope or to otherwise perform a calculation that suggests what the minimum suitable strength may be that can provide therapeutic benefit.

The measure used to assess a person's response to stimulation during screening assessment can also be a biometric measure, an optical measure such as a measure obtained from pulse oximetry or NIRS measurements from one or more locations on the patient's scalp. The absolute or relative change, or change over a time (e.g., rate of decay) for an NIRS signal measurement may be used to assess or confirm a minimum stimulation strength that is above a threshold level that is required to produce a defined change in the patient.

In embodiments, the length of an interval after a treatment is supplied during which the patient shows a change in a measure that is different than that measure obtained for a baseline interval (which occurred before the stimulation was given) can be used to assess sensitivity to TMS (and appropriateness of using stimulation strength within a selected range which may include a subthreshold level of stimulation). A "rebound time", may be defined as the interval over which the brain settles back or returns to pre-stimulation baseline value (or a value that is not statistically different from a baseline normal range). In embodiments, the rebound of a measure can be assessed after a 30-60 minute TMS treatment session has occurred and may be assessed within an hour after, or hours or days after the stimulation has occurred. Alternatively, the rebound time can be measured after only a short interval of stimulation has occurred (e.g., 1-2 minutes of stimulation) and may reflect the brain's "responsiveness" to stimulation such as stimulation below a selected threshold level (e.g., MT). The rebound time may be also assessed by examining a change in a task performance (e.g., reaction time or Go/NoGo accuracy measure) or any change in the amplitude/latency of an evoked potential, or QEEG measure that occurs as time passes after the TMS is provided.

In an embodiment, one example a screening test criterion being assessed as per steps 59 or 80, occurs as follows. Baseline energy at a test frequency of the posterior EEG (e.g., 7 Hz) is assessed. TMS is provided at 7 HZ and then energy at 7 Hz of the posterior EEG can be tracked after the pulse train stimulation is completed. The time it takes for the energy at the test frequency to return to the pre-stimulation level seen in the amplitude spectrum is associated with the sensitivity or "rebound time" of the brain to the stimulation. Additionally, rather than measuring EEG power at a frequency of the stimulation, other measures can be assessed over time such as coherence (at the same test frequency or different frequency), a brain measurement associated with treatment benefit, or other measure. Alternatively, the screening test can assess the amount of time which is required before a TMS related change in a sensed objective measure or change in a subjective reported measure, relative to pre-stimulation baseline occurs.

In an embodiment, a method of providing combination transcranial magnetic stimulation treatment to a patient comprises providing a first transcranial magnetic stimulation treatment protocol of Type 1 treatment 40-48 in a clinical setting during at least a first set of treatment intervals using a first transcranial stimulation device in a clinical setting that provides a first type of magnetic stimulation therapy transmitting a first transcranial magnetic stimulation signal having a first magnetic field strength that meets a first treatment threshold which is determined to be above a patient's motor threshold; and establishing a second stimulation treatment protocol for Type 2 treatments (e.g., 52, 54, 56) during at least a second set of treatment intervals using a second magnetic or electrical stimulation device that is used remote from said clinical setting and that provides a second type of stimulation therapy using a second stimulation signal having a second field strength that is set to be below the first treatment threshold. For example, the treatment is applied to a patient suffering from a psychiatric disorder such as depression, and the treatment protocol designed for the treatment of depression. This combination treatment with TMS may be selectively provided only to a patient who previously passed a screening assessment procedure by demonstrating a motor threshold that was determined to be at a selected low stimulation strength that indicates increased likelihood that low level TMS (e.g., provided by a permanent magnetic) is suitable to provide treatment benefit. In embodiments, advantages can be realized such as the second magnetic field strength can be provided by a second device and is sufficiently low that the magnetic stimulator of the device does not require liquid cooling. Another advantage is that by using the second type of treatment the interval between each of the first set of treatment sessions may be increased compared to what is used in the absence of the second treatment protocol in order to decrease the inconvenience by decreasing the frequency of clinic visits.

The strength of the stimulation used in the second stimulation treatment protocol can be defined in several manners. It may be provided at strength that is subthreshold (e.g. <MT) for a particular patient or for a reference group of patients. The second field strength may also be selected as at least sufficient to produce a change in a patient's cardiac measure (e.g., heart rate, an ocular measurement, a time-locked change in the optical measurement (e.g., NIRS measurement related to brain activity/bloodflow), or a measure associated with parasympathetic nervous system arousal state. In an embodiment, the first treatment protocol includes TMS at least five times a week during an induction interval and is followed by the second protocol that includes TMS every other day, or less, during a maintenance interval.

Dual-Phase Therapy Devices and Protocols

Neurostimulation using energy in electrical, ultrasonic, magnetic, or other modalities has been shown to have promise in the treatment of various disorders or to provide desired changes in mental or physical states (e.g., improved alertness, focus, or sleep). Systems and methods that are relevant to, and can be realized as part of, the invention include systems providing modulation of biological tissue to achieve various advantages. For example, the following are incorporated by reference herein for all intents and purposes as if recited fully herein: U.S. application No. 20190255346, entitled "Magnetic stimulation coils and ferromagnetic components for treatment and diagnostic procedures"; U.S. application No. 20180071544, entitled "Magnetic stimulation coils and ferromagnetic components for reduced surface stimulation and improved treatment depth"; U.S. application No. 20140012064, entitled "Reducing discomfort caused by electrical stimulation"; U.S. application No. 20190247654, entitled "Apparatus and methods for predicting therapy outcome"; U.S. application No. 20140249352, entitled "Transcranial magnetic stimulation system and methods"; U.S. application No. 20140235928, entitled "Central base coils for deep transcranial magnetic stimulation"; U.S. application No. 20140179980, entitled "Systems and Methods for Neuro-EEG synchronization therapy"; U.S. application Ser. No. 20/090,204015, entitled "Systems and Methods for Depression Treatment Using Neuro-EEG Synchronization Therapy"; U.S. application No. 20190224490, entitled "Methods and systems for preventative migraine headache treatment"; U.S. application No. 20180345032, entitled "Method and apparatus to record and analyze TMS treatments and results", U.S. application No. 20190201707, entitled "Method and system for therapeutic brain stimulation using electromagnetic pulses", US20190209855A1 filed by Helekar and Voss entitled Method and apparatus for providing transcranial magnetic stimulation (TMS) to an individual, and U.S. application No. 20040122281, entitled "Means and methods for treating headaches". Additional art that is relevant and which is also incorporated by reference, includes systems and methods for providing transcranial alternating current stimulation (tACS), transcranial direct current stimulation (tDCS), and sonic energy for brain stimulation. For example, U.S. application No. 20190232059, entitled "Targeting Alpha Oscillations with Transcranial Alternating Current Stimulation (tACS) for the Treatment of Major Depressive Disorder (MDD)" U.S. application No. 20180272129, entitled "Targeted Steerable Transcranial Intervention To Accelerate Memory Consolidation", U.S. application No. 20170224990, entitled "Apparatuses and Methods for Neuromodulation", U.S. application No. 20160129237, Entitled "Electrode Assemblies for Delivering Therapeutic Electrostimulation", U.S. application No. 20150174418 entitled "Device and Methods for Noninvasive Neuromodulation Using Targeted Transcranial Electrical Stimulation", U.S. application No. 20150088224, entitled "Wearable transdermal electrical stimulation Devices and Methods of Using Them", and, U.S. application No. 20120209346, entitled Transcranial Stimulation.

Clinical TMS therapy is conventionally realized and reimbursed using a course of treatment that occurs 5 days a week for 4-6 weeks and which may be followed by a tapering of about 6 treatments once or twice a week. Although additional TMS treatment may be provided due to symptom relapse, it is done sparingly due to the cost of the treatment which is performed in a clinic. For at least a portion of patients, this restricted approach, which does not provide a second type of therapy (e.g., maintenance therapy), may not provide meaningful benefit, produce less benefit than desired, may not sustain benefit, or may have other unwanted results. Additional benefit may be obtained using combination therapies with two or more devices and/or stimulation protocols as is disclosed.

Support for Systems and Methods using Dual-Phase Treatment

Stimulation using subthreshold (<MT) TMS stimulation provided by rotating permanent magnets did not demonstrate statistically significant and clinically meaningful improvements in clinical studies (e.g., NCT02839798; NCT01370733) such as for treatment of major depressive disorder (MDD). Since <MT stimulation does not deliver as much energy as suprathreshold (>MT) stimulation it may not be sufficient to serve as a primary, stand-alone therapy in at least some subjects. Although the mechanisms for stimulation <MT therapy are unclear, magnetic and electrical stimulation at lower intensities has shown to induce a number of changes in the brain. Several lines of evidence support providing lower levels of therapy in an ongoing manner will provide benefit. For example, low level maintenance therapy provided regularly can extend, and even improve, the amount of therapy benefit over time.

Not to be limited by theory, some examples of the benefit of ongoing, regular neurostimulation are now provided which do not use TMS and which are not related to the treatment of MDD. Although some examples, and the associated results, are not related to TMS therapy or therapy for MDD, these findings support advantages, and otherwise inform embodiments, of the dual-therapy treatments disclosed herein. These are applicable to improving therapy with TMS (for MDD or other disorders) over that which is conventionally practiced. In some instances symptom improvement from daily lower level TMS stimulation may take 6-12 months or longer.

Example #1: responsive neurostimulation with implanted neurostimulators for treating epilepsy shows incremental improvement over long periods of time with repeated treatments. Responsive neurostimulation for the treatment of epilepsy (e.g., using technology disclosed in U.S. application No. 20100137937, entitled "Modulation and Analysis of Cerebral Perfusion In Epilepsy and Other Neurological Disorders" and U.S. application No. 20030028072, entitled "Low frequency magnetic neurostimulator for the treatment of neurological disorders") has shown long-term, progressively improved clinical benefit as the duration of treatment (and total number of repeated treatments) increases with the trend extending out to 9 years (Nair, D. R., Laxer, K. D., Weber, P. B., et al. *RNS System LTT Study* (2020). *Nine-year prospective efficacy and safety of brain-responsive neurostimulation for focal epilepsy. Neurology,* 95(9), e1244-e1256). There are also observations by the inventor related to migraine treatment. This showed that it was possible to prophylactically decrease the incidence of migraines compared to what occurred when stimulation was only provided responsively (due to migraine onset) by daily provision of even a few pulses (e.g., 8) which is a much lower amount of energy than is commonly delivered by clinic-based TMS treatments. These data show that in addition to a discrete period of stimulation therapy providing benefit, large symptom improvements are obtained from repeated, daily neurostimulation. Increased benefit may require that stimulation occurs regularly over long periods of time (e.g., months or years).

Example, #2: In the treatment of disorders, there is a delay from the start of treatment until benefit is seen and it may take between 2 and 12 weeks before initial symptom benefit is obtained. Similarly, in pharmaceutical treatment of various disorders, there may be a delay of several weeks for benefit to appear even though daily administration of the medication is typically used for the treatment regimen. In other words, continuous treatment may require varying amounts of time before benefit is seen and this interval may be several months. A non-responder at 8 weeks may become a responder at 12 or 16 weeks if the initial cycle of stimulation (i.e., induction) is extended or supplemented by maintenance treatments even if these may be less frequent or use a lower stimulation intensity.

Example 3: Although TMS only uses an initial interval of treatment, the use of continued maintenance has been shown in other treatments to be important since without this regular stimulation the therapeutic benefit can disappear. Further, lower amounts of stimulation that occur with maintenance stimulation which is less frequent and provides less of an electrical dose than occurs in induction is not itself sufficient to produce a robust treatment response that occurs by first using a more intensive (e.g., more frequent or stronger signal) induction therapy protocol.

Not to be limited by theory, TMS treatments that occur in the clinic at >MT intensity levels may not be effective since these do not occur with sufficient frequency or for sufficient duration to provide a sufficient "dose" of brain stimulation. Providing supplemental at-home treatment that modulates neural activity either directly or indirectly (e.g., via stimulation of peripheral nerve targets) between clinic visits may serve to provide the additional reinforcement required for a positive treatment outcome to occur and to subsequently be maintained. In embodiments, TMS therapy provided in the clinic may be stronger than that supplied at home, and further, the latter may be subthreshold with respect to generation of action potentials or motor threshold.

Without being limited by theory, data from various scientific and clinical studies related to electrical or pharmaceutical intervention of the brain or body can be interpreted to support that:

A) during an initial induction period stimulation should occur sufficiently frequently for benefit to emerge and if decreased therapy is given during this time there may be a smaller clinical benefit or no clinical benefit realized both during the induction interval or afterwards;

B) electrical/magnetic stimulation may have a "dose response" similar to that seen with pharmaceuticals. More frequent stimulation and/or stronger stimulation may produce a therapeutic response that is not seen when too low a "dose" is provided (e.g., functional neurostimulation "dose" can be a function of stimulation strength across a time interval), while too much stimulation should be avoided if that leads to tolerance or unwanted side-effects;

C) electrical/magnetic stimulation parameters should be sufficient for an individual and may require titration for individual patients;

D) maintenance schedules and protocols for TMS may need to be adjusted to reflect individual variability (e.g., ranging from 3 times per week to once a month) and may be individually set based upon subjective or objective measures meeting a defined treatment criterion or by trial-and-error of maintenance schedules with patient feedback;

E) when using a combination of two stimulation protocols realized in an interleaved, simultaneous, or sequential manner, adjustments to the first protocol may result in adjustments to the second protocol, in relation to considerations such as total "dosage" of delivered neurostimulation;

F) providing stimulation with lower strength at regular intervals between the provision of treatment with higher strength stimulation may reduce risk of habituation/tolerance/unwanted side-effects compared to that which may occur with frequent higher-strength brain modulation;

G) subthreshold therapy may only be suitable for long term therapy in some patients who meet a treatment criteria (e.g., those who show increased sensitivity to treatment such as improvement above a certain level by 4-6 weeks, etc.), In an embodiment, a method of providing magnetic stimulation therapy comprises providing a combination of a) a first magnetic therapy type using a stimulation intensity which is above a threshold level such as the level required to produce a motor response in a person (e.g., 110%-120% MT) and b) a second magnetic therapy type that occurs using a magnetic field that is lower in strength than the first therapy. The lower strength stimulation can be repeatedly provided to supplement the higher strength therapy that occurs in a clinic and may occur in a location outside of a clinic such as in a patient's home. Even if a home-based TMS system can provide supra-threshold stimulation, the second stimulation type either alone or in combination with supra-threshold stimulation may be advantageous and lead to less habituation or tolerance.

Exemplary Combination Treatments

In embodiments, as shown in FIG. 2, a first TMS therapy type is provided periodically and the interval between sessions is selected to be within a range of once or twice a day, week, or month. For example, the first TMS therapy may comprise therapy sessions of between about 20 to 60 minutes which occur 5 days a week (at least initially for an "induction" treatment) during a treatment course lasting about 3 to 6 weeks. The TMS treatment may occur in addition to medication or psychotherapy, or both. A second TMS therapy type then occurs. It is provided according to a second schedule e.g., selected from a range of twice a day to once a week. The second TMS therapy can occur at a stimulation strength (or total energy when integrated over time) that is less than that provided using the first TMS therapy. For example, in the treatment of depression the second TMS therapy may occur in 30- to 60-minute sessions scheduled for 5 days/week, or two thirty minutes sessions which occur daily and are separated by a minimum of approximately 6 and 12 hours. In embodiments, the device that provides the second therapy may have a treatment limit rule that constrains how often the treatment stimulation can be provided during an interval such as a day or week. The first or second therapy may be provided in combination with a software ecosystem that provides cognitive, behavioral, or cognitive behavioral therapy such as antidepressant software-based therapy (e.g., e-mental software health care program).

In embodiments, as part of the transition between a first and second therapy type (e.g. between sessions 48 and 50 of FIG. 2), or at least after the first therapy type if the second type of therapy will not occur, there is be provided a transition or gradual "taper" period rather than an abrupt termination of an the initial course of treatment provided as induction therapy which occurs prior to a transition to maintenance therapy. For example, a taper period after TMS induction could involve a 3-2-1 pattern such as once per 10 days for about one month, twice per month for 2-3 months, once per month for 3-4 months. The schedule of the tapering treatment, can be adjusted based upon assessment of data such as neuroimaging, patient profiles, changes in QOL surveys etc.

In an embodiment, the stimulation treatment of FIG. 2 utilizes at least one repetitive TMS/rTMS device that produces a pulsed magnetic field of more than 1 tesla by passing a rapidly-changing current through a coil. The repetition rates of TMS may normally range from theta to low beta (e.g., 4 to 20 Hz) or may exceed higher. Additionally, at least one lower strength device that utilize lower stimulation rates such as 1 Hz, or even a single pulse or two pulses provided within a 15 minute window, can be used as part of a maintenance or Type 2 therapy such as has been shown to provide benefit in the treatment of migraine. Lower strength devices may also provide subthreshold stimuli at higher rates (e.g., 30-100 Hz)

Stimulation Strength Selection.

The supra-threshold level can be defined as the minimum value needed to cause a response in a target muscle when stimulating the motor cortex of an individual, known as the motor threshold (MT). In embodiments, TMS strength is set relative to the minimum intensity of the magnetic field necessary to elicit a response above a stimulation threshold level (e.g. >MT). Without being limited to theory, the assumption of relying on the MT for setting the level to be used during therapy is that excitability in non-motor cortex is similar to that of motor cortex, or at least highly correlated. MT has become commonly relied upon for determining TMS dose due to its relationship with safety such as the possibility of inadvertent evoking of seizure, and due to its efficacy and reproducibility in stimulating cortex. In embodiments the suprathreshold strength of the field for the first magnetic therapy is set at, or 5%, 10%, 15%, 20% or 25% above motor threshold, but preferably in the range of 10-20%.

In embodiments, MT in a resting muscle (Resting MT; RMT) can be determined visually or using analysis of electromyography data (EMG). The International Federation of Clinical Neurophysiology (IFCN) has defined RMT in two manners. The first uses an ascending relative frequency method to find the "level which induces reliable motor evoked potentials (MEPs) in 50% of 10-20 consecutive stimuli" which are typically found to be in the range of 100 uV (Rossini et al., 1994). Alternatively, the methods may use a descending method to find a level at which an MEP of at least 50 uV occurs in at least 50% of 10 to 20 consecutive trials (Rothwell et al., 1999). The use of EMG to determine MT providing a quantitative measure of muscle response which does not require subjective interpretation by the patient or practitioner and is known as the "EMG-MT". In embodiments, the system 100 of FIG. 6 can have a stimulation/sensing module 112 that is configured with EMG sensing. The step of determining suprathreshold stimulation for a stimulation session can be done as part of the treatment sessions shown in FIGS. 1 and 2.

In an alternative embodiment, motor thresholds can be detected visually. This can occur either alone or in combination using EMG of the right first dorsal interosseous (FDI) using the relative frequency method. For example, a 50% frequency criterion is used to determine MT and with the intensity beginning at a clearly suprathreshold intensity. The motor threshold for EMG can be defined as the lowest setting of TMS machine power at which ≥5 out of 10 MEPs were ≥50uV peak to peak. Alternatively, for the visual observation of muscle twitch (OM-MT) OM method, MT can be defined as the lowest setting at which, for example, at least 5 out of 10 stimuli resulted in any observable movement of the index finger.

In an alternative embodiment, rather than/or in addition to using MT, the measure that defines the stimulation level that is used for at least the first TMS protocol can be the threshold amplitude which evokes a minimum change in a biometric measure such as cardiac activity (e.g., decrease, increase, or change in heart rate, or heart rate variability), skin conductance, reaction time, reaction accuracy, eye or pupil activity, responsiveness, or tracking accuracy assessed using ocular measurement techniques.

In an alternative embodiment, the threshold used by the stimulation protocol for at least a first or second type of TMS protocol can be selected as the minimum amplitude (or repetition rate or other stimulation characteristic defined by the stimulation protocol) which causes a minimum desired physiological change to occur in a measure such as pupil dilation, a characteristic of saccade measurement, blood pressure, or other measure associated with modulation of the sympathetic or parasympathetic nervous system. Measures may also include measurements or changes in measurements from baseline for measures that include reaction time, respiration rate, galvanic skin response etc. Measures used to set threshold for stimulation strength and stimulator location can also be calculated using multivariate measures with weightings related to the patient and or disorder being treated.

In embodiments, the stimulation strength for the second TMS protocol can be defined as a) a selected percentage below that used in the first TMS protocol, b) a subthreshold level that is not considered to be sufficient to evoke an action potential but that is selected to meet a criterion of being sufficient to evoke a biometric or physiological response. Alternatively, the strength of the stimulation signals may be adjusted using a different formula which includes imaging data. The second TMS protocol may use a stimulation strength that is not adjustable and is simply lower than that used by the first TMS protocol.

In an embodiment, TMS devices and stimulation protocols can be classified as two types. The first type is a "strong therapy" device, which can provide fields generally above one Tesla, with pulses having relatively longer intervals, and rates that can be set at 5, 10, 15 Hz, or higher. Strong therapy devices can provide rTMS at rates above 5 Hz using stimulation field strengths above MT. Additionally, a second TMS stimulation type includes "low strength" devices that produce fields that are below 1 Tesla, and/or are above 1 Tesla but have a very short pulse durations such that these are below MT.

In embodiments the first type of TMS is delivered by a "Strong therapy" device and the second type is supplied by a "low strength" device. In an embodiment, the second TMS therapy uses a field that is generated by one or more magnets or electromagnets which produce a field of approximately 6,000 to 8,000 Gauss (i.e., 0.64-080 Tesla at the surface of the brain).

Additional Combination Protocols and Screening Assessments

Figure 3:
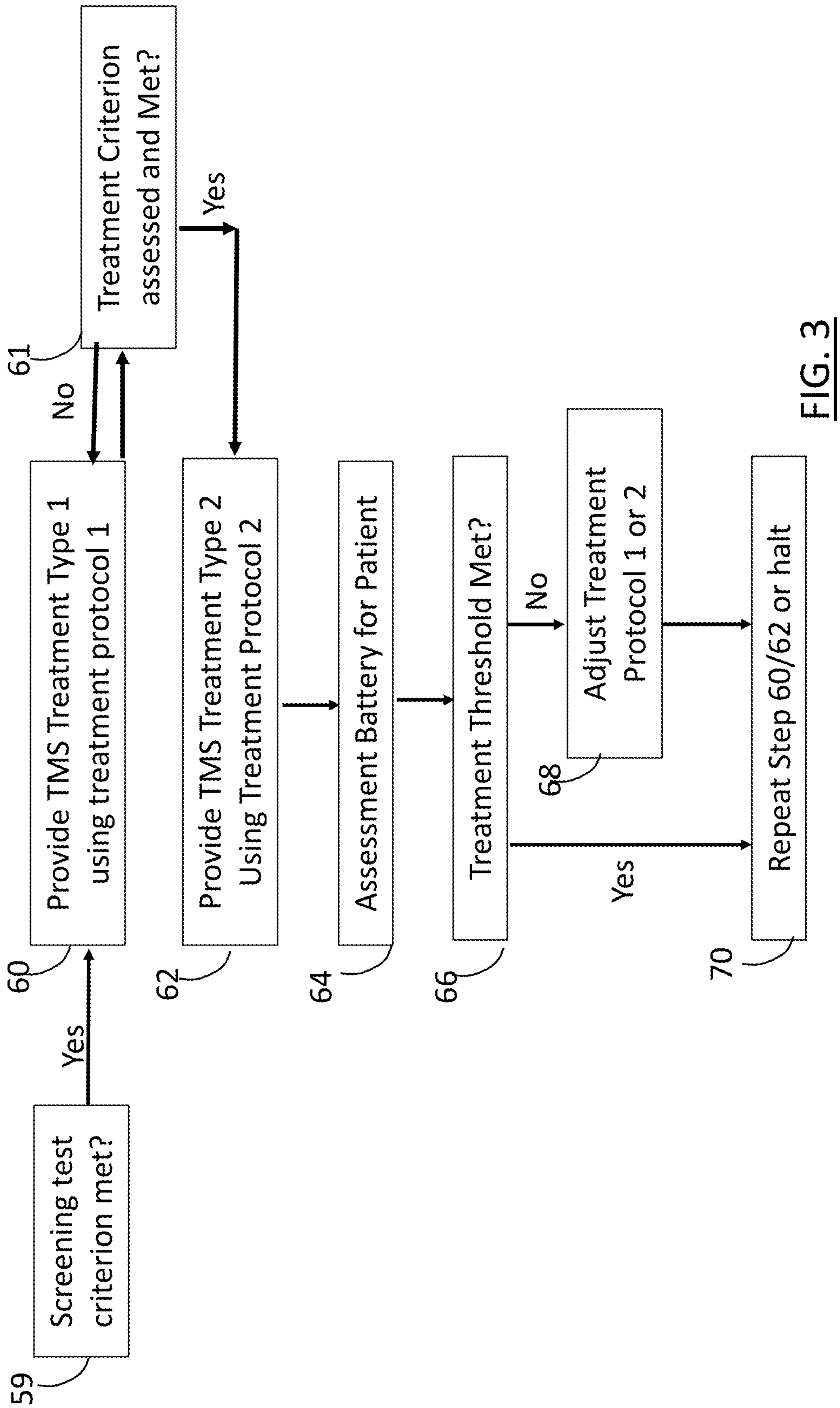
FIG. 3 shows a method of contingently adjusting a treatment protocol based upon screening and treatment criteria.

FIG. 3 shows an embodiment of a method starting that may start with step 60 if a screening assessment 59 does not occur prior to therapy start. In step 60 a first type of TMS treatment is provided (e.g., one or more sets of treatment sessions occur such as those related to an induction interval). If a treatment criterion is assessed 61 and is met (e.g., a selected number of sessions have occurred or a patient shows a positive treatment response result when a selected measure is compared to at least one treatment criterion) then the method moves on to step 62 wherein a second treatment protocol is provided. This may be a maintenance treatment provided by a second type of TMS treatment (e.g., providing a series of maintenance treatment sessions). However, if the treatment criterion is assessed 61 and is not met, then the induction interval is extended and the first type of TMS treatment is continued. In embodiments, the second TMS treatment type uses a stimulation field strength that is lower than that used in Type 1 treatment. For example, Type 1 TMS treatment is provided with a strength that is at or above the MT of the patient, while Type 2 TMS treatment is below that threshold due to reduced pulse amplitude, repetition rate or width, such that the field power integrated over time is less. In embodiments, the method includes periodically reverting to step 62 and providing a treatment Type 1 in step 60 (i.e. booster treatments at higher strength fields are provided to maintain therapy benefit).

In step 64 an assessment battery is used to evaluate the patient. This may include collection and assessment of at least one subjective or objective measure or a combination of the two types of measure. For example, an improvement on a depression scale compared to what the patient reported at a prior time (e.g., baseline prior to starting therapy) may be required to meet a treatment threshold criterion in order for the Type two treatment to continue without adjustment. Alternatively, neuroimaging data can be assessed using modelling, discriminant, or other type of analysis. For example, brain network analysis and/or source localization algorithms such as VARETTA or LORETTA analysis, or brain network modelling (e.g., Structural Equation Modeling (SEM)/path analytic modelling) may be used to determine if treatment criteria have been met and a positive treatment result has occurred due to an improvement in a measure relative to baseline.

In step 66 the assessment battery results are compared to treatment criteria such as thresholds to determine if these are met (positive treatment result) or not met (negative treatment result). If treatment criteria are not met ("No"), then in step 68 the protocols for Type 1 or Type 2 treatments are adjusted before returning to step 60 or 62 as defined in the treatment regimen, or as determined by physician evaluation of the assessment battery results. Alternatively, if the treatment criteria are met in step 66, then the method flows ("Yes") to step 70 without adjustment of the treatment regimen and associated stimulation protocols and parameters. In step 70 the method can return to treatment type 1 or treatment type 2, as per the defined treatment regimen. Alternatively, an interval of days, weeks or months can occur prior to repeating steps 60/62, or the method can stop and the treatment is halted permanently either due to failure of treatment or because the treatment has created an apparently lasting change and treatment is no longer needed.

In embodiments, as has been disclosed earlier the combination dual-phase TMS therapy is used only for patients who have passed a screening test criterion 59 which may be provided prior to and/or after a first treatment session (e.g., See 40 of FIG. 2), and indicates the patient may be an appropriate candidate for combination treatment with low-strength TMS. Other examples of the screening assessment are provided throughout this specification, such as for FIG. 4.

FIG. 4 shows an embodiment of a treatment method which includes determining if a patient is a candidate for a treatment using only type 1 treatment, or a hybrid therapy which combines both Type 1 and Type 2 treatments, and which can also be used to initially set the treatment protocols. In embodiments both Type1 and Type2 treatments use TMS. In step 80 the patient is assessed with respect to least one screening criterion such as minimum sensitivity to TMS as reflected by detection of a defined response. For example, the response can be detection of a change in measure when stimulated using a selected stimulation parameter value related to TMS field strength (e.g., amplitude, pulse width, etc.). In the case where the patient meets one or more screening criteria then the next step of their treatment 82*a* is to provide Type1 treatment using protocol 1 for a selected interval (or number of treatments) after which the patient either simply transitions to TMS type 2 treatment 86, or undergoes an assessment 84 with a treatment criterion to determine if a) the patient has met a treatment criterion and is ready to move to TMS type 2 treatment or b) should follow path ("No") and continue with Type 1 treatment 82*a*. Alternatively, if the patient fails at least one screening criterion in step 81, then the treatment moves along step 82*b* where TMS Type 1 is provided rather than providing combination therapy.

In further alternative embodiments, after TMS Type 1 is provided in step 82*b* according to a protocol for a defined set of treatments, the method then returns to step 80 and patient is re-assessed to determine if a change has occurred which allows a patient to now meet screening test criteria (which may be the same or different than the criteria used on the prior screening session(s). In other words, after a patient has undergone a course of treatment their suitability for combination therapy may be assessed positively.

Alternatively, not all steps of a method must occur in order, or at all. For example, the screening step 80 can be defined to only occur after one or more treatment sessions have been provided using TMS type 1 treatment in step 82*b*. Additionally, screening assessment in step 80 can included comparing a measure of a subject taken both before and after TMS therapy provided with Type 1 stimulation in step 82*b* to asses whether a stimulation related change (relative to baseline) meets a screening criterion. The stimulation provided during steps 82*a*/82*b* as part of treatment may be different than TMS stimulation provided as part of the screening test step 80. For example, the stimulation that precedes a screening test may use a stimulation protocol that occurs over the course of a day with periodic assessment of measures.

As shown in FIG. 5*a*, a combination therapy protocol 90 is provided which comprises providing a first stimulation treatment protocol 92*a* and a second stimulation treatment protocol 92*b*. The method may be used to realize the treatment sequences shown in FIGS. 1 and 2. As such the steps of the combination therapy 90 that is provide occur as defined in a treatment regimen protocol. In an embodiment both therapies are provided using TMS.

In an embodiment, the first protocol 92*a* provides modulation of brain tissue and the second protocol 92*b* modulates activity in one or more of the cranial nerves, which in turn may have central effects. For example, the first stimulation treatment 92*a* of the first stimulation protocol may define a coil-based TMS treatment. The first stimulation treatment 92*a* provides stimulation fields which are sufficiently strong to meet or exceed a first defined threshold (e.g., >MT) that corresponds to providing suprathreshold stimulation of brain tissue. A second stimulation treatment 92*b* is weaker and is configured to provide stimulation of the brain or cranial nerves at amplitudes that are insufficient to directly provide suprathreshold stimulation of brain tissue (e.g., are below motor threshold). In embodiments, the two treatments 92*a*, 92*b* are typically provided at two non-overlapping intervals, such as can occur sequentially with the first occurring during an induction interval and the second during a maintenance interval. Alternatively, the two treatments 92*a*, 92*b* can occur in an interleaving manner such as when the second treatment provides supplemental stimulation at intervals between the first treatment 92*a*.

In embodiments, the combination therapy 90 comprises a combination of a first and second treatment 92*a*,92*b* that is provided during an interval using a combination a first treatment 92*a* that comprises magnetic stimulation and a second treatment 92*b* that comprises TDCS or TACS. In an embodiment, the first therapy is TMS and a second therapy provides electrical stimulation.

In embodiments, combination stimulation is provided using a) a magnetic stimulator that is positioned to provide suprathreshold or subthreshold stimulation of at least one cranial nerve, and b) a second stimulation therapy that provides stimulation with a set of 2 or more electrode stimulators which provide either TDCS or TACS. Although each of the two types of stimulation signals may not effectively or robustly stimulate the cranial nerve when used in isolation, by combining magnetic stimulation (which may be incapable of suprathreshold stimulation that consistently evokes an action potential) with the TDCS or TACS, the stimulation can become effective, or more effective, at modulating the activity or excitability of the cranial nerve. Without being limited by theory, the first stimulation may serve as a priming stimulus (i.e. increase responsiveness to stimulation, or decrease the minimum amplitude of a signal needed to effectively modulate the neural tissue) for the nerves so that these are more responsive to the fields of the second type of stimulation, or vice versa. In embodiments, combined therapeutic modulation (e.g., synchronized magnetic and electrical stimulation) can also be directed towards spinal and peripheral targets.

In embodiments, the first stimulation treatment 92*a* is magnetic stimulation that is provided to a brain or cranial nerve target, or both, simultaneously. Alternatively, the first stimulation treatment may include electrical stimulation of the vagus nerve (using an implanted or external device) using a protocol that is designed to provide complementary stimulation using a second stimulation 92*b* which is magnetic stimulation of a cranial nerve located above the neck.

In an embodiment, therapy includes using a conductive element is implanted or injected into a location below the scalp and adjacent a cranial nerve. The magnetic stimulation is then applied to the nerve with the implanted conductive member serving to enhance the effect of the field stimulation of the target cranial nerve. The implanted conductive member may also incorporate at least one diode at one end the conductive material, or between two conductive elements.

In embodiments, the combination therapy 90 includes using least a first and second stimulation treatment 92*a*,92*b* to provide indirect stimulation of at least two different regions of the brain (or a single region of the brain is stimulated indirectly using two afferent channels) by stimulating a combination of targets which include at least two different cranial nerves. For example, the first stimulation treatment 92*a* may stimulate an occipital nerve or third occipital nerve (which may be useful in the treatment of occipital headache/neck pain), in combination with a second stimulation treatment 92*b* that provides stimulation to the supratrochlear nerve to modulate different brain regions (or one brain region using two different inputs). When the stimulation is magnetic it may be provided at either a suprarelati or subthreshold strength. In embodiments, subthreshold is defined as at least one of a) below the level required to initiate an action potential in the cranial nerve, b) below the MT threshold of the brain tissue located below the cranial nerve.

In embodiments, a combination therapy 90 includes a first stimulation treatment 92*a* that is directed primarily influence a frontal brain region and a second stimulation treatment 92*b* that is directed to primarily influence a non-frontal region of the brain, and the stimulation is applied to at least two different cranial nerves for indirect modulation of the frontal and non-frontal regions, respectively.

In embodiments, a combination therapy 90 includes providing indirect stimulation of a frontal and non-frontal region of the brain, using two different cranial nerves respectively with a first stimulation treatment 92*a* and a second stimulation treatment 92*b* which are designed to be implemented during the same time interval and to cause two brain regions to be stimulated in a synchronized manner, or in an asynchronous manner (e.g., stimulation energy is provided to cause the target brain tissue of the two regions to be stimulated out of phase).

In embodiments, a combination therapy 90 is defined to comprise a first stimulation treatment 92*a* which is the TMS stimulation that is applied to the head and a second stimulation treatment 92*b* which is TMS or electrical stimulation of a spinal cord target (either at the same time or sequentially). In the treatment of pain, modulation of both central and peripheral targets, at the same time or sequentially may assist in retraining the thalamocortical circuit, or other communication between other brain networks, decreasing symptoms. In embodiments, dual-phase TMS can be used in the treatment of spasticity, motor disorders, pain disorders and other disorders which involve control of, or feedback from, the peripheral nervous system activity and/or muscle movement/disorders. Traumatic brain injury (TBI) with, or without, motor dysfunction can be treated by the invention.

In embodiments, as shown in FIG. 5*b*, an assessment of data for a patient 94 is performed which leads to contingent adjustment of a treatment protocol which is provided 96. The assessment is used to improve the suitability or effectiveness of the treatment that is provided by adjusting it for each patient. In an embodiment, an assessment step 94 occurs which determines the best protocol parameters to use to stimulate at least one target (e.g., brain target or cranial nerve), and then a first therapy is adjusted to use at least one TMS stimulator that is located over at least one brain target or cranial nerve location. For example a cranial nerve location can be determined during the assessment 94 using imaging or other procedure (e.g., electrical transcutaneous nerve mapping). Assessment of a patient can also include genetic, biochemical, or other assessment using biomarkers that have been found useful in setting stimulation parameters or determining suitable candidates for treatment. In an embodiment, the stimulator transducers are then contingently adjusted 96 so as to be configured to stimulate locations defined in relation to locations of an individual's notches/foramina (e.g., any of the 21 foramina in the human skull). In an embodiment the stimulation protocol and stimulation parameters are assessed to determine parameter values that successfully lead to minimum changes in biometric measures such as cardiac activity, ocular/pupil activity or responsiveness, or change in EEG or evoked potentials.

In embodiments, a first stimulation treatment 96 includes stimulation of at least one cranial nerve such as a trigeminal nerve, a supraorbital nerve (medial or lateral branch), a supratrochlear nerve, a facial or nasal nerve, mandibular nerve, great auricular nerve, auriculo-temporal nerve, lacrimal nerve, occipital nerve (greater or lesser occipital nerve), or third occipital nerve. In some embodiments, step 94 is skipped, or may only occur prior to the first stimulation treatment of an individual, or occurs periodically (e.g., every 1 or 6 months), but does not occur prior to every treatment.

As shown in FIG. 5*c*, in embodiments stimulation treatment occurs according to parameters defined for a treatment regimen protocol in step 97. The patient is then assessed 98 using at least one of subjective (e.g., QOL instruments) and objective (e.g., QEEG) measures. The assessment 98 may include comparing result data to data obtained prior to stimulation or baseline data obtained at a prior date in to determine whether the treatment has produced changes a set of measures indicating absence or presence of treatment benefit. Additionally, the therapy protocol can define stimulation that is provided during the assessment 98 which is different that provided during therapy such as providing stimulation that is used to determine the stimulation parameter values that will cause the stimulation to be above the person's motor threshold (this can also occur instep 94 of FIG. 5*b* where the assessment includes providing stimulation used to calibrate the stimulation subsequently delivered for therapy). In step 99 the treatment may be adjusted contingently based upon the outcomes of the assessment. The contingent adjustment may be accomplished using a treatment algorithm, a set of rules that cause adjustments based upon the assessment outcomes, a look-up table which maps treatment parameter value adjustments to assessment outcome or based upon other operations which may be carried out due to assessment by a doctor or suitably trained technician. The adjustments in treatment protocol can be related to any treatment parameter of a treatment session or to parameters that define a series of treatments.

Combination Treatment Systems

FIG. 6 Illustrates an embodiment of a system 100 including control subsystem 102 which interacts with a user by controlling a user interface module 120 realized with hardware (e.g., keyboard or touch sensitive screen) and software configured to display information and accept user input. The control system 102 contains the stimulation protocol defined for at least one device and allows user adjustment of the protocol. In embodiments, the modules of the system 100 can be realized within the housing of a device 100*a*, or can be provided in a distributed manner across several devices with connection or communication with third party instruments (e.g. a set of EEG bioamplifiers). The control subsystem 102 can be realized using a customized computer such as a laptop, tablet, or smartphone and includes all the hardware and software components typically found in modern computer devices including processors that operate an operating system to run software programs, clocks, timers, storage memory, database functionality, wired/wireless communication (cellular, WIFI and Bluetooth), transducers for providing visual, auditory, and/or vibrotactile stimuli and information, display monitors, and the like.

At least a first stimulation device 104 is configured for providing neurostimulation (e.g., a TMS system) to a patient using a first type of stimulation. The system may also include, communicate with, or include the use of a second stimulation device 106 which provides TMS stimulation at a lower strength than the first stimulation device, or which is a device that provides electrical stimulation treatments (e.g., tDCS or tACS). At least one of the devices 104, 106 is configured for providing therapy and communicating with the control subsystem 102, and either local (e.g., in a patient's room) and remote (e.g., outside of the room) system components such as a computer physician computer 116. The Control subsystem 102 and other subsystems, modules, and components of the system 100, are shown separately in the figure but can share resources and be realize wholly or partially within the housing one of the stimulation devices 104,106 or other system component 108, 114, 116, 117.

In an embodiment, the devices 104,106 or other system component communicate using a computer network 108 (i.e., a LAN or the Internet) using its communication module 110 having a wireless transceiver which communicates wireless signals with a patient device 114 such as a patient's smartphone device. A computer network 108 can be used by the communication module 110 to communicate with user devices and system components that may be in the same room or remote from the stimulators (e.g., 108, 114, 116). The system 100 has a stimulation and sensing module 112 to provide additional stimulation (e.g., electrical) of a user and for sensing data related to a user (e.g., evoked potentials). The sensing also allows user monitoring by system components and/or by medical devices and sensors that can obtain sensed data, such as physiological measures, and which are configured to communicate with the system 100. Sensed data can include, for example: measures of brain activity such as electroencephalography (EEG) data, QEEG, and evoked potential data; electrocardiogramata; cardiac data (e.g., heart rate (HR), heart rate variability (HRV), and blood pressure) sensed by ECG electrodes, optical sensors, or blood pressure cuffs; electrical data related to muscle or nerve activity, ocular activity, etc. The ECG data can be obtained by an instrument using a bioamplifier that operates ECG electrodes which is then communicated to the system 100.

A wearable 117 accessory such as wrist-worn medical device with a watch-form factor can be configured to monitor, for example, blood pressure, blood oxygenation (SpO2), pulse, or physiological measures and can also communicate with the system 100. Wearable accessories 117 and/or the patient/physician programmers 116 can be realized as tablets or wearable devices such as smartwatches and fitness tracking/health monitoring devices with bracelet form factors that are provided with software applications that enable communication with the system 100 and which can provide input signals that are used to adjust the stimulation signals provided by the stimulation devices 104/106. The patient physician programmers 116 can also be realized as customized wearable devices that are provided with buttons for user interaction, sensors, and alerting capabilities for vibration, sonic, visual alerting. Ear stimulation/sensing devices can also be used to sense brain, cardiac, temperature or other data, to stimulate the auricular nerves including branches of the vagus nerve, and/or to communicate with users using sonic signals. The system 100 can communicate with one or more wearables 117 which can be at least one device worn by a patient on their body such as wrist, leg, or other body worn device. The wearable can allow interaction with the user and also may monitor blood pressure, blood oxygenation ($SpO_2$), pulse, temperature or other data. The stimulation system 100 can control and communicate with sensors or devices such as wearables 117 to provide stimulation or sensing through stimulation/sensing module 112 and can communicate through the communication module 110. The EEG of a patient can be used to adjust the stimulation protocols and parameters provided by stimulators 104/106.

The system 100 includes a power module 118 with battery and/or which can use mains power for powering all system components including the stimulation devices, a control module 102 for controlling the stimulation devices as well as other system components used to provide therapy, a user interface module 120 for communicating with a user and accepting user input data, and providing alerting signals to users about provision of therapy. The communication module 110 is configured for transmitting and receiving data signals in a wired or wireless manner (i.e., via a wireless communication signal connection of the computer network 108) between itself and system devices such as a wearable 117, a physician/patient programmer 116, or at least one router/modem such as a wireless router of the network 108 that serves as a wireless access point (WAP) that allows the device 104/106 and other system components access to a wireless local area network (WLAN) to communicate with each other, the internet, or a remote computer network. A computer network 108 can include, or communicate with, a hospital network that can allow data communication between the device 104/106 and other system components such as a user/data server 122 where data related to sensing or stimulation can be transmitted, processed, stored, displayed, and shared with to other system components. For example, data signals related to the provision of treatment or sensed data can be transmitted from a patient's home through the computer network 108 to a patient or doctor mobile device 116 such as smartphone or wearable. This allows a doctor to remotely monitor or adjust the operation of the device 104/106 or obtain patient data. At least one of the devices 104/106 can communicate with a wearable 114 such as a smartwatch to send the user reminders about providing treatment according to a defined schedule which can be helpful when TMS is provided in a home environment.

In an embodiment, the user/data server 122 can be incorporated into, or share data with, an electronic medical system that tracks data related to a patient. Accordingly, when the system is used for providing TMS patient monitoring a nursing station or physician device 116 may display information on each of a set of patients which includes data such as: number of treatments a patient provides each week, what day the treatments are scheduled on, survey data, physiological measures, cardiac activity measures such as blood pressure and heart rate variability, medication type and dosage, and other information related to the patient's health which may be collected by a care or service provider.

The control subsystem 102, device 104/106, computer network 108, the user/data server 122, wearable 117, and any other system component include a the necessary memory (e.g., RAM, ROM, PROM, EPROM, FLASH), realized as a memory chip or other computer-readable medium for storing computer executable instructions (i.e. software code) to be operated upon by one or more processors to execute computer-executable instructions for performing the operations, functions, steps, methods, etc., described herein. The system and network components can be realized, in part using customized remote controllers or smart devices (e.g., physician/patient programmer 116), one or more general purpose computers or special purpose computers (e.g., a server or group of servers working together "server farm").

The system can be integrated to share data of the electronic medical records (EMRs) of a patient which can be implemented as part of, or shared with, the User/Data Server. The computer network and wired/wireless communication can include or incorporate an internet-accessible wireless communication network, and preferably, over a wireless wide-area network (WWAN) such as a mobile telephone data network including (for example, based on a Global System for Mobile Communications (GSM) or Code Division Multiple Access (CDMA) cellular network or associated wireless data channels). For compliance with medical regulations, for example HIPAA, communication across the networks are preferably conducted securely.

In an embodiment, the system 100 is designed for the provision of treatment using clinical-based TMS with at least one TMS stimulation device 104. However, the first or second treatment device 104/106 can also be realized as a portable or wearable device that is related to the providing treatment with electrical or magnetic energy. Treatment may be provided for many types of disorders or conditions including addiction, drug/opioid abuse, high blood pressure, cardiovascular, metabolic or psychiatric disorders, anxiety, migraine, headache, sleep, sleep apnea, stroke, cognitive, movement disorders including tremor and Parkinson's. Stimulation can also be provided to promote health and wellness such as improvements in mood, focus, mental operations, sleep, energy, memory or executive functions. The wearable accessory can include wearable stimulators that may stimulate peripheral nerves such as the vagus or cranial nerves. Devices which may be designed to stimulate locations which have been found to create desired changes using acupuncture or electro-acupuncture can be incorporated into the system 100 and are considered within the scope of the claimed invention. These also include devices configured to modulate inflammatory response, cardiac activity, or appetite of an organism, and other conditions treated by "electroceuticals".

In embodiments, the treatment of medical disorders, states, or conditions with TMS, behavioral support is provided by an ecosystem module 124. In embodiments, ecosystem module 124 is realized as part of a Tracking, Reminders and Devices (TRD) module 126, and includes software modules, media, and content for providing behavioral coaching, tracking, and prompting/promoting behaviors (e.g., smoking cessation; reminders to operate software used to provide therapy for cognitive or psychiatric disorders). These the ecosystem module includes videos, information, and graphic animation that provides instructions, educational content. The software can provide connection for online chat or video support such as technical support or counselling. This can also be supplied via a link to a website which provides these services through a web browser. In the treatment of depression, symptom and activity tracking can be provided by a remote patient device 114 configured to track and measure this and also to relate this to amount or timing of smoking, eating, taking medication, etc. (i.e., the features module can be realized in part within the patient device 114 or wearable 117. Activity measures such as eating can be recorded, for example as an electronic diary. Virtual behavioral, cognitive, or cognitive-behavioral coaching associated with first line therapies can also be provided by the ecosystem module 124 such as providing focusing/attention exercises for ADHD treatment, or nutritional and/or food recommendations and reminders, for example when related to weight loss programs. Videos and instructions can also be provided by the ecosystem module 124 for addiction treatment or other disorder. Further, The ecosystem module 124 can support features can also be provided such as weblinks to virtual support groups (i.e., chat groups/discussion boards) or software can enable virtual meetings with physicians or support groups to occur. Stimulation protocols can be tied to various aspects of the ecosystem features such as prompting the user to provide stimulation if analysis of user input suggests this is merited or desired (e.g., the user has indicated they will be eating dinner in 2 hours and stimulation is provided to decrease appetite). In treatments which include magnetic stimulation of the spine such as for the treatment of pain, the ecosystem may serve to remind patients to do physical therapy exercises that are designed to reduce pain and strengthen muscles.

If a user stops providing at-home therapy for several days or weeks then it can be helpful for a physician to be notified and able to review a user's stimulation history to understand a pattern of therapy decrement or date of halting therapy. In embodiments, the TRD module 126 operates a "stopped therapy" protocol which prompts the patient to input information about what caused the therapy attenuation. For example, a patient is provided with a notification on the patient programmer 116 such as "You have stopped using your device for at least X days" or "you have selected 'ignore' the last x-times when notified to start therapy". The notification is followed by a first set of user input choices related to provide context such as being queried about whether this is due to: A) a technical problem; B) change in symptoms; C) on vacation or other life event, or D) other. A second set of user input choices will be invoked using a logic tree structure or rules established in a database module 128 or lookup table, so that they are contingently presented based upon user input responses to the earlier set of choices. For example, if the user selected "B" then the protocol would contingently ask the user to select from a plurality of more specific reasons such as: A) symptoms are better; B) symptoms got worse, C) no change in symptoms. This user surveying continues as defined by rules or lookup table defined in TRD before being sent to a physician or other designated contact for review by the communication module 110.

The individual modules/subsystems of FIG. 6 are provided with all the hardware, software program instructions, algorithms, circuitry and power that are required to provide the functionality as disclosed herein. Modules may share resources of other modules. For example, both the ecosystem module 124 and the communication module 110 may perform hardware and software operations related to sending a wireless notification signal. At least one control module 102 controls the other modules of the system 100, and controls the provision of therapy according to parameter value settings of a therapy protocol. The control module 102 contains the circuitry needed to control the other modules including at least one processor, readable and writeable memory, timers, clocks, signal processing circuitry, and all circuitry that is typically included in a device such as smartphone. The circuitry of a smartphone may serve as the control module for a device 104/106 if it is configured to be attached to, and controlled by, smartphone (or smartwatch or other wearable tech) which interfaces with the device 104/106 to control the remaining modules and hardware of the device 104/106. The user interface module 120 includes displays (e.g., LCD or LEDs, touchscreen) and associated circuitry for presenting text, image information, notification signals, and a graphical user interface for obtaining user input. Notification signals can be presented using other sensory modalities such as sonically (e.g., using a speaker), and a microphone allows processing of voice commands by the user interface module 120. For example, tone signals or recorded voice messages can be provided to a user by the module 120. Notifications can be multi-modal and presented both by the device 104/106 and the user device 114. The user interface module 120, provides at least one user control for allowing adjustment of therapy (e.g., turning therapy on/off or increasing/decreasing stimulation intensity). As disclosed, in embodiments, control signals provided by a user in the form of gestures, voice commands, are processed by the user interface module 120 and used to control system 100 operation.

Communication between system components can occur under the communication module 110 using any suitable wireless protocol including for example, radio frequency, WIFI, IEEE 802.1, Bluetooth, infrared-based, sonic-based etc. Identity verification mechanisms can prevent crosstalk or identification issues such as when two devices are used to communicate with a device as is well known. Unique transmission wavelengths, encryption, ID, handshaking, and time-sharing schemes are well known.

The system 100 operates to provide, assess, detect, and store therapy events. Therapy events are any event related to the provision of therapy, such as, the start and completion of a therapy session and the associated parameters that were used as well as a log of intensity changes, user input data provided by a user interacting with the system components to turn a device on or off, or users response to surveys completed by a user according to a schedule. Therapy events are tracked, logged, and counted by the TRD module 126.

In an embodiment, the system 100 or device 104/106 is designed with a stimulation/sensing module 112 that causes stimulation treatment protocol of the treatment regimen module 130 or stimulation or sensor location to be adjusted or otherwise operated upon. The adjustment can occur due to evaluation sensed data that can guide the treatment or adjust the stimulation protocol as may occur by the evaluation module 132 which has signal analysis and statistical programs for assessing the data from the stimulation/sensing module 112. For example, the evaluation of impedance occurs according to an impedance protocol defined for a stimulation protocol. For example, stimulation may be intermittently paused while impedance is assessed (or this can occur continuously while stimulation is provided) to ensure the impedance is within a defined normal operating range for stimulation treatment to be provided as intended. The impedance can be tested at the beginning of each therapy session, or can be tested intermittently, such as every minute, or every 5 to 10 minutes, during the provision of therapy. Impedance can be measured for one or more stimulators or sensors such as an EEG electrode and the user can be warned if the values are too high. Sensing can also be used to asses stimulator location or orientation on a user's head or body, and can include sensing visual information sensed by a video source or 3d positioning technology. Some types of sensor status may be assessed during calibration routines to ensure proper connection or arrangement with respect to a patient, such as: a pulse oximetry signal from a pulse oximeter sensor; location/orientation of at least one magnetic transducer (e.g., coil) in relation to a patient's head; location/stability of one or more near infrared reflectance spectroscopy (NIRS) sensors; and, eye tracking systems for assessing pupil, saccade, or other ocular measures. Sensor data can be used to assess quality criteria. For example, pressure sensor data obtained from a pressure sensor may by used to assess if sufficient pressure exists between the device and the user's head, back, or other portion of the body. If assessment of sensor data indicates that an adjustment is needed (e.g., impedance does not meet a quality criterion) then a stimulator/sensor quality criterion failure operations occur, such as the user is alerted to adjust a sensor/stimulator. In an embodiment, the criteria values or ranges that indicate successful stimulator/sensor assessment are stored in the system 100, and within the device 104/106, and the measurements associated with each treatment session are stored in the memory of the device or system.

Closed Loop, Rule-based, and Guided Therapy Adjustment

In embodiments, the devices 104/106 and system 100 are configured to provide therapy based upon evaluation of reference data, sensed data, or a signal serving to provide feedback data that is used to guide the provision of treatment and adjust the stimulation protocol. The evaluation of these data and/or generation of the feedback data that can guide the treatment or adjust the stimulation protocol may occur by the evaluation module 132 which has signal analysis and statistical programs for assessing the data. The feedback data is real-time or recent data, such as pre- and/or post-stimulation sensor or user input data, and may also include assessment of historical feedback data such as summary or trend data. For example, as shown in FIG. 5*c*, stimulation treatment is provided according to a therapy protocol 97. Feedback data is obtained and assessed 98 and used to contingently adjust the treatment protocol 99 according to defined treatment criteria or rules. In an example, if patient input indicates symptom improvement that exceeds a selected amount or which occurs for at least a selected interval (e.g., 2 months) and that is assessed as meeting a treatment criterion 98, then an adjustment in the treatment protocol is made 99 such as the therapy duration or number of treatments per week may be adjusted (e.g., increasing inter-session interval). Alternatively, if a trend of increased benefit is determined to level off or decrease in step 98, then in step 99 the treatment protocol is adjusted to increase a schedule or duration of treatments for therapy Type 1 or Type 2. In an embodiment, the treatment adjustment rules for operating upon feedback data lead to outcomes based upon whether the data meet one or more therapy criteria as assessed in step 98. The therapy criteria can be assessed using single result values of feedback data, or upon summary statistics, calculated scores, or trend statistics, and may be multivariate.

Feedback data can also be used in real time to adjust the stimulation protocol based upon sensed data. The system 100 can comprise at least one sensor in communication with the stimulation & sensing module 112 for obtaining sensed data (e.g., brain or heart data, etc.) and a user interface module 120 for allowing patients to input data. The sensed data or patient data serves as feedback data and the control subsystem 102 is configured to operate software to assess 98 and operate based upon the feedback data. The evaluation of feedback data provides device adjustment (or proposes adjustment to a user) of one or more parameters of the treatment protocol 99 for at least a first or second stimulation type. The feedback data can include electrical activity related to muscle or nerve activity of the patient, MT related data, or other sensed data from a sensor of the stimulating/sensing module 112. The feedback data may include patient input data input by a user via the user interface module 120, which is related to subjective assessment of pain, depression, addiction, or other disorder or unwanted symptom.

In embodiments, TMS can be provided with the objective of causing a desired change is a brain activity measurement or a change in a parameter of a modelled brain network. The assessment of the response to the TMS, may be an absolute change, a relative change, or a difference between a measurement (e.g., EEG/QEEG, reaction time, subjective score) assessed both at baseline and after or during treatment TMS. In embodiments, detection of certain stimulation evoked changes can be used to select and prescribe a medication. In other words, TMS can be used as a screening tool for selecting appropriate patients that may respond to one or more medications: a positive treatment response to a selected TMS protocol may be associated with successful response to a particular drug or drug class. Accordingly, in FIG. 5*c*, step 99 may include selecting or adjusting medication based upon assessment of data 98 obtained in response to the provision of stimulation 97.

In an embodiment, a method of treating pain in a person comprises an assessment 94 that includes assessing or locating a region that has been a source of pain for the person (e.g., lower back). In step 96 a treatment target location for brain stimulation by TMS is determined using supra-threshold stimulation which is related to the region of pain. Additionally, the stimulation parameters (e.g., location, field strength, stimulation pattern, etc.) may be adjusted according to assessing a measure of pain (or assessing a decrease in a measure of pain compared to a baseline sample) of the patient, wherein the measure is either reported or measured from the patient. rTMS field pulses at the supra-threshold stimulation can be administered to treat the target location to reduce pain. Additionally, the stimulation parameters can be adjusted based upon an assessment 98 of the size or duration of a change in the EEG (or other measure) that is measured during an interval after TMS is provided. In an embodiment, after supra-threshold stimulation is used to define a suitable brain target and or provide treatment of that target, this is followed by lower intensity stimulation parameters being adjusted and used to treat the pain based upon information obtained by the supra-threshold stimulation. Accordingly, either suprathreshold assessment and response to supra-threshold treatment can be used to guide adjustment of TMS delivered with lower intensity stimulation.

In an embodiment, a treatment method includes a) an assessment step 94 which includes setting and iteratively adjusting the stimulation parameters (e.g., location, field shape, strength, repetition rate frequency, pulse duration, or orientation etc.) until a desired change in a measure is detected (e.g., a heart rate or ocular measure), and then b) setting the stimulation parameters used for stimulation with a lower intensity based upon that assessment and proving treatment 96. In an embodiment, the location of stimulation can be used by the lower intensity of stimulation and the frequency of stimulation can be set 96 according to a characteristic of the patient's pre- or post-stimulation EEG, such as peak frequency within at least one selected EEG band of the patient. In embodiments, this procedure is done as part of a screen test 80 of FIG. 4, wherein a change must be detected for certain ranges of a parameter that are assessed. For example, only patients who show MT at a stimulation intensity that is below a selected level are candidates for treatment with a Type 2 TMS therapy provided at a lower-range 82*a*, otherwise they are treated only with coil-based TMS in step 81.

Figure 7B:
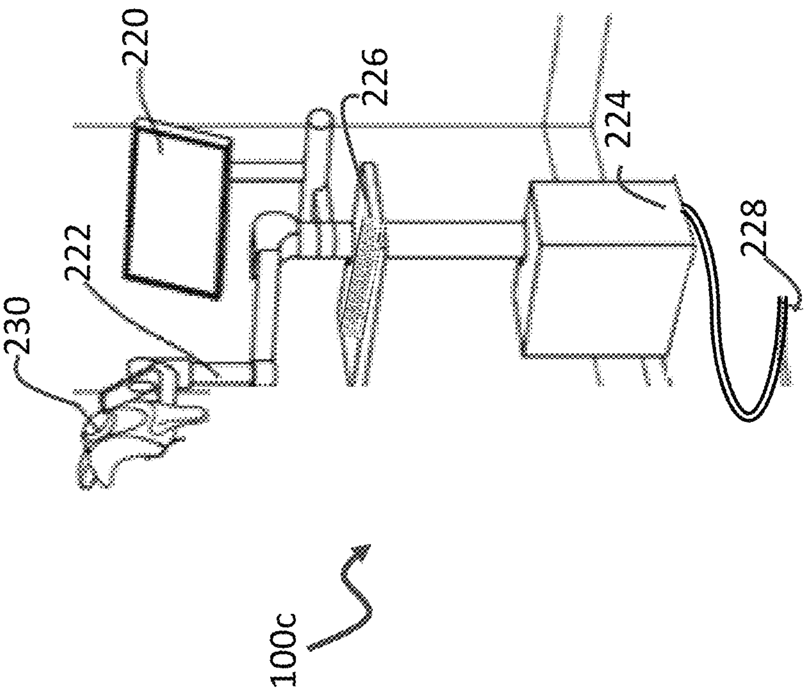
FIGS. 7*a*-7*b* show two types of systems for providing TMS therapy.
Figure 7A:
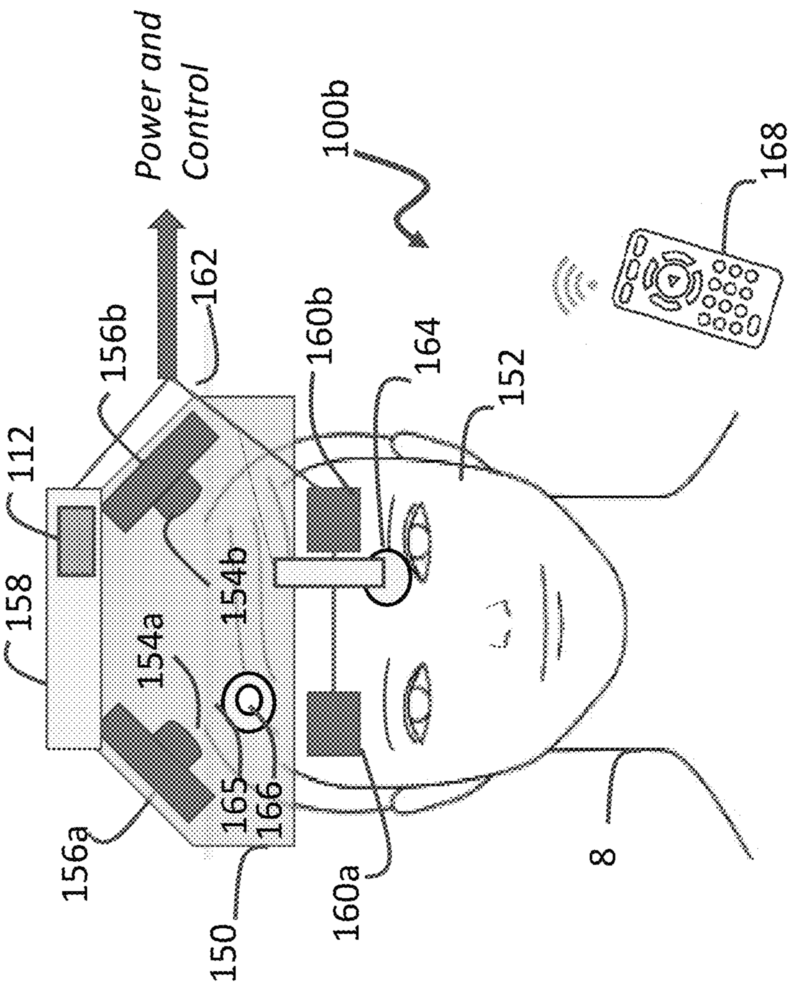

FIG. 7*a* shows a system for providing TMS which includes a housing 150 configured for positioning upon, or securing to, a patient's head 152. The housing provides at least one magnetic stimulator 154*a*, 154*b* (e.g., a magnetic coil stimulator with associated electronics or a permanent magnet that is rotated to produce an oscillating magnetic field) that is secured to the housing 150 by a positioning member 156*a*, 156*b*. In embodiments, if the magnetic stimulators 154*a*, 154*b* are TMS coils then the positioning members allow for adjustment of location and angle of the stimulator as well as for electrical connection of the stimulator 154 to the control subsystem 158 (which has power and control circuitry necessary for controlling the stimulation/sensing module 112 to provide magnetic stimulation according to a stimulation protocol). If the magnetic stimulator 154 is a permanent magnet, then the positing member 156 also contains a motor for causing the permanent magnet to rotate during the provision of therapy as well as means to adjust angle and location of the stimulator. The control subsystem 158 controls a stimulation/sensing module 112 to provide magnetic stimulation via the magnetic stimulators 154*a*. It can also, or alternatively, provide electrical signals (e.g., tACS) to stimulator/sensing pads 160*a*, 160*b* which are sent along an electrical conduit 162 (such as a multistranded conductive wire) that provides for electrical connection (or which may be used to communicate control, data, and power signals between the module 112 and other sensor such as NIRS). Stimulator/sensing pads 160*a*, 160*b* can also be used to record EEG data using the module 112. The housing 150 may also provide a video camera 164 which may be self powered (i.e., battery powered) and which communicates with, and is electrically connected to, the control system directly (using electrical conduit 162) or indirectly by wireless communication, and can monitor a patient's eyes during stimulation to obtain ocular activity measurements. In embodiments, the electrical conduit 162 is attached to at least one of the control subsystem 158 circuitry of the housing 150, other control, sensing/stimulation, and power modules of the system 100, or both. Although the system 100*b* may have user input controls supplied on the housing 150, a user controller 168, such as a smartphone with wireless or wired communication and customized software can exist as part of the control subsystem 158 and can provide user control and viewing of stimulation parameters through communication with the circuitry provided in the control subsystem module 158 of the system 100*b* or in the communications module 110. The system 100*b* may also be realized and incorporate prior art TMS systems which are customized to provide the features disclosed herein.

In embodiments, the system 100*b* includes is a helmet/cap containing one or a number of magnetic stimulators, and the number, location and orientation that can be varied to provide customized neurostimulation programs according to an individual's attributes, anatomical data, and needs. A handheld controller 168 allows the user to adjust the stimulation provided. For example, in embodiments, the controller 168 directs the precise timing, pulse characteristics, durations, and strength, orientations, spread, shape, and locations of the magnetic pulses and fields (including individual fields and fields created by the summation of fields) generated by individual magnetic sources.

In an embodiment, the helmet contains one or more magnetic shields 165 located between the magnetic stimulators and the scalp surface of the user 8. The shields can include conductive material that is formed to constrain the shape/size of the field that passes below the shields and into the brain or body of a patient. The shields can contain at least one shaped aperture 166 and be configured with conducive or shielding materials that shape or focus the magnetic field. In embodiments, shaped shields conform to the scalp of a patient and can be used with conventional coil-based stimulators to shape and constrain the fields and/or to allow individualized adjustment of the fields for a selected individual.

Figure 9:
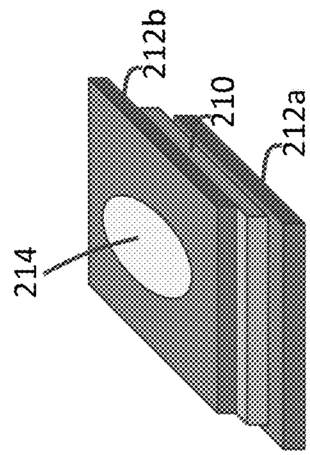
FIG. 9 shows a partial perspective view of a magnetic shield.

In embodiments, a shield that blocks electromagnetic or radiofrequency energy is constructed of an insulating and conforming material such as silicone, rubber, or cloth and contains 1 or more coils or layers of conductive mesh, foam, sheet, or screen. FIG. 9 shows a shield having a first and second insulating layer 212*a*, 212*b*, that flank a conductive mesh 210 and through which an aperture 214 has been formed which allows magnetic fields to pass. The conductive layer may or may not be grounded using a conduit of the stimulation/sensing module 112. The conductive material can be formed using copper, steel, a conductive fluid or ink or metallic dust or particles, metallic alloy or a magnetic material. The shield can configured with 1 or more regions that pass magnetic fields while other regions are configured with material that absorbs, attenuates, or redirects the energy emitted by the magnetic stimulators to limit a characteristic of the energy that reaches the tissue of the user, such as the total amount or shape/area of energy. The shields may be shaped with different thicknesses of conductive material in different areas, and may have variable attenuation characteristics (e.g., a mesh is formed with different areas having different conductivity). This allows different regions of the shield to attenuate the energy that is directed towards a user by a variable amount based upon spatial location of the energy. This shielding enables a customized energy "mask" to be provided that is tailored to the target of the stimulation energy. In addition to providing increased localization of the stimulation field that modulates tissue of a patient, use of stimulation masks may enable a higher strength of field to be used since the field the reaches the tissue of a patient is being applied to a more focused and discrete area. Stimulation masks may also be useful when one or more coils creates a diffuse field that is not well adjusted to selectively activate a single nerve target or other desired target area without significant co-activation of other tissue. Using a mask that has one or more physical or non-conductive apertures (i.e., non-shielded regions) can be used to shield certain non-target areas while allowing magnetic field energy to pass through and stimulate one or more targeted areas of the brain, spinal cord, cranial nerves, or other peripheral nerves or other target tissue. In addition to passing or attenuating magnetic fields, the shields can be configured to deform, focus, or otherwise shape the magnetic energy as it passes. In an embodiment the TMS device includes a head mounted device with a shield that is mounted to a motor and which is shaped with 1-4 fan blades (or a rotating disk that has EMF/conductive shielding or an aperture formed within a portion of its surface) so that the rotation of the shied sequentially allows and blocks a field emitted by a permanent magnet according to the speed of rotation.

In an embodiment, a TMS device includes a helmet (or head mounted device) configured with at least one magnetic stimulator for applying a magnetic field to a head of a subject, and the helmet (or head mounted device) comprises: a housing configured to receive or otherwise engage at least a portion of the head of the subject; and the at least one magnetic stimulator includes at least one of: i) a coil for providing electromagnetic stimulation, and ii) a permanent magnet assembly within said housing, with an assembly comprising: a first motor coupled to at least one first permanent magnet by a first axle having a first axis of rotation, wherein the first axle is configured to permit movement of location and/or rotation of the first permanent magnet; and, a first adjustment mechanism configured to permit spatial and/or angular adjustment coupled to the first coil or permanent magnet, wherein selectable adjustment of the adjustment mechanism allows adjustment of at least one magnetic stimulator with respect to the patient's head.

In embodiments, the selectable adjustment of the adjustment mechanism occurs independently for at least one magnetic stimulator (e.g., permanent magnet) relative to the housing.

In embodiments, the selectable adjustment of the adjustment mechanism occurs contingently for a first magnetic stimulator based upon at least a second magnetic stimulator relative to the housing. For example, positioning members 156*a* and 156*b* are configured so that movement of one positioning member contingently adjusts, or requires user adjustment of, the position or angle of the second positioning member.

In embodiments, the magnetic stimulator comprises a permanent magnet that may be operated upon by a coil and electromagnetic circuitry to generate a stronger field than the permanent magnet otherwise would. In embodiments, this stronger field remains <MT.

In embodiments, a second type of magnetic stimulator may be configured to provide type 2 therapy with a field that is 0% to 5% or 5% to 20% below a patients MT. In embodiments the Type 2 TMS stimulator is configured to provide a field strength of 100-150 microtesla and frequency 1-30 Hz with between 2 and 8 magnetic stimulators.

In embodiments, during an assessment step 94 of FIG. 5*b*, the positioning member 156 is configured to allow adjustment of the magnetic stimulator for subsequent therapy step 96 to occur according to a position determined using a first TMS therapy (considered assessment) and is based upon a location that was confirmed as being a successful treatment location. Accordingly, a location and/or angle found to be successful for the first TMS therapy can be relied upon to adjust the stimulation protocol for the second TMS therapy. In an embodiment, the first TMS therapy and second TMS therapy share a coordinate system, or the coordinate system for the first TMS device is mapped to a coordinate system for the second TMS device to allow proper adjustment of the of the second TMS device. In an embodiment, the first TMS therapy device provides suprathreshold stimulation and the second TMS therapy provides subthreshold. In an embodiment, instead of a permanent magnet, an electromagnetic coil is used to provide a stimulation field of less than 1T or which is less than that required to reach the MT of an individual.

FIG. 7*b* shows an embodiment of the system 100*c* in which is an office-based system for providing TMS therapy. This includes a video display 220 (e.g., touch sensitive display) for allowing a medical practitioner to view, select, and adjust data related to the therapy program including the stimulation protocol parameter values. A keyboard 226 having a touch sensitive mousepad can also allow user input and control of a computer 224 which runs an operating system and software and has customized hardware so that it serves as the control subsystem 102 of the system 100*c*. A power cord 228 is connected to appropriate isolation circuitry and is used to power the computational and stimulation coil and electronics of the system 100*c*, including at least one magnetic stimulation coil stimulator 230 (with required stimulation circuitry) that is positioned and oriented using a control arm 222. The system is configured to work with monitoring devices which permit collection of sensed data related to physiological, biometric, and positional information related to the patient (e.g., using sensors as disclosed for FIGS. 6 and 8).

Figure 8:
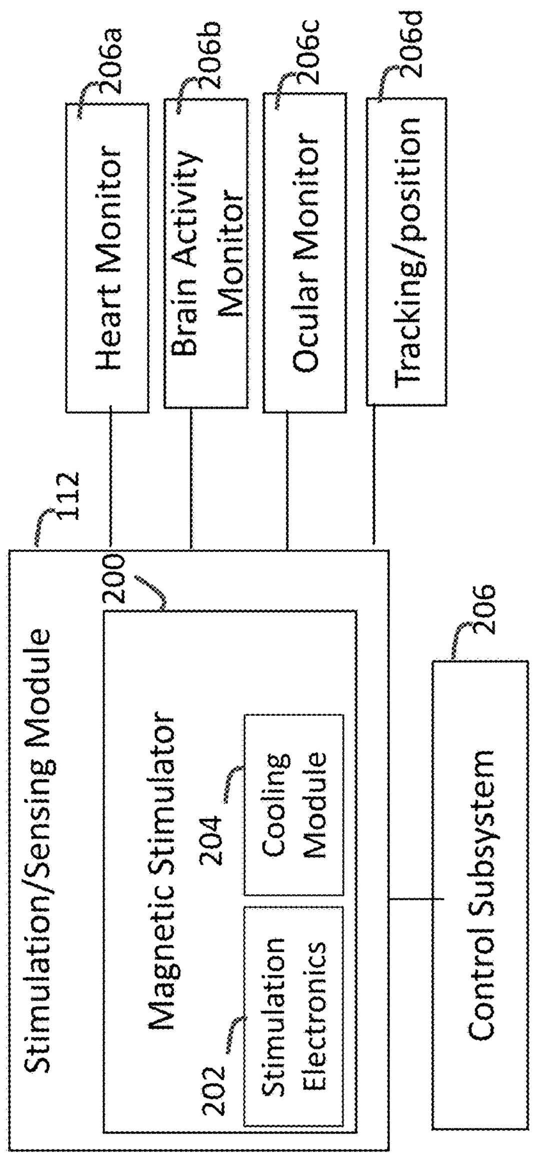
FIG. 8 shows system components associated with providing stimulation, sensing, and positioning of stimulators and/or sensors.

In embodiments, the sensing/stimulation module 112 of the system 100 can include a magnetic stimulator device 200 which drives one or more coils of the stimulator using stimulation electronics 202, and is cooled by a cooling module 204 as shown in FIG. 8. The stimulation electronics 202 can include a power source that drives charging circuitry for powering one or more capacitors which are attached to one or more switching elements for driving one or more magnetic stimulation coils. The stimulation electronics 202 also contain safety circuitry. The cooling module 204 can provide for liquid and/or air-based cooling of the electronics and coils of the module 200 and may also have temperature sensors for monitoring and contingently adjusting the stimulation and cooling operations such as may occur if the coil temperature exceeds a defined limit. As shown, the stimulation sensing 112 module is configured with a control module 206 to provide control and power of sensor devices, or communicate with sensing devices, including sensors for monitoring heart measures 206*a* (e.g., ECG, pulse oximetry, blood pressure), brain activity (e.g., EEG, NIRS) 206*b*, ocular activity 206*c* (e.g., digital video capture and analysis software), and tracking/positioning of the stimulators and sensors (e.g., 3D positioning software that works on digitized spatial information) 206*d*.

Use of Virtual/Augmented Reality for Setting Position Protocol Parameters.

Across a series of cycles of TMS treatments, repeatable positioning of magnetic stimulators may be important for consistent stimulation of an intended brain region. Methods that use anatomical landmarks as fiducial locations for the magnetic stimulator placement may have errors if the landmarks are visually identified. The use of anatomical landmarks may also be unreliable due to individual variations across subjects or the technician's skill in accurately identifying the landmarks or placing the stimulator. To overcome this unreliability, an augmented reality (AR) visualization-based TMS guidance system may be used and provided by the user interface module 120 in conjunction with a patient/physician programmer 116.

In an embodiment, a TMS guidance system which provides AR visualization assists manual TMS coil positioning. For example, after a patient's face is scanned and registered using an RGB-D or other 3D camera (of user interface module 120 or positioning module 134) to capture a 3D spatial map of the patient's head (and at least one marker on the magnetic coil). Then the positioning module 134 provides an AR representation of the one or more prior or "reference" positions from a previously created 3D spatial map of the patient's head. This is visually overlapped on a video display with one or more current markers (e.g., the current position of the TMS coil, the location on the head where the TMS field will be maximum, or the location on the head which is the target). In the next step, the technician then adjusts the current position marker with the prior position marker until these overlap. Accordingly, the system can guide the user to position the TMS coil with high repeatability. The use of AR allows head and coil co-registration, hotspot/grid alignment and registration of a location on the head associated with a MEP, a location where stimulation evoked changes in an objective measure occurred at a low stimulation intensity. Co-registration provided by the positioning module 134 can include coil position, pitch, yaw, and roll (i.e., position and 3d angle) and may also include assist in providing adjustment of the stimulators in a helmet worn at home by a patient and allow for adjustment helmet stimulators.

In an embodiment, the positioning module 134 provides for creating and utilizing a digital three-dimensional representation of a patient's head for providing accurate TMS treatment and comprises: a magnetic stimulator (e.g., coil); an image sensor; and a processor configured to generate a fitted head model using a predetermined head model in combination with feedback data from the sensor, the head model is a generic head model, a previously created head model of the patient, or a module created from neuroimaging/imaging data of the patient created from at least one of: magnetic resonance imaging (MRI) image information, x-ray image information, or computer tomography (CT) image information of the human subject. The head model may also include a predefined or previously used location where motor threshold was calculated, a location defined by NIRS or physiological data, a functional location such as a location for which stimulation creates an evoked change.

In embodiments, the positioning module 134 permits combining non-invasive transcranial stimulation navigation data with functional imaging data (that may have been collected previously and resides in the database, modelling, and statistics module 128. The positioning module 134 can employ a method comprising the steps of: acquiring an anatomical image data of a brain, acquiring brain activity data of the brain, co-registering at least a portion of the brain activity image data and anatomical image data, said portion being associated with a portion of interest of the brain which is a target for neuromodulation, and positionally aligning the combined view of the brain with transcranial magnetic stimulation (TMS) coil position/orientation using 3D navigation software of the system which may be realized using augmented reality or computer visualization software that can superimpose the coil position with the anatomical target. Further, the adjustment can occur either manually or robotically, and the system can include motors and actuators that are controlled by the system processor to adjust the position and other characteristics of at least one magnetic stimulator (e.g., the position and angle of the control arm 222 components and the stimulator 230 as shown in FIG. 7*b* can be controlled).

In embodiments, software therapy can be provided before or after TMS to promote treatment of disorders such as MDD by augmenting, supplementing, or sustaining the improvements caused by stimulation therapy. Software-based therapy can be provided by the ecosystem module 124. For example, the Emotional Faces Memory Task (EFMT), is a cognitive-emotional software treatment that is delivered using an "App" on a computer platform. This serves as an example of electronic mental (e-mental) health care for depression. The combination of software and neurostimulation therapy may not only serve to provide the benefit of two therapies, but also the software-based therapy can reinforce brain stimulation (and vice versa).

In an embodiment, a method for classifying a patient profile into a psychiatric category includes providing fMRI data to a processor that operates an algorithm of a database, modelling, and statistics module 128. The processor of the module 128 operates an algorithm configured to derive from the fMRI data relevant network modelling information including, for example, brain region functional connectivity information or other metrics extracted from the fMRI data. The method also includes using the network modelling information for classifying a psychiatric profile (e.g., biotype), or a related probability of the profile's classification for the patient by applying a classifier or discriminant function and providing, by the processor, a psychiatric profile classification or probability of the patient belonging to a defined psychiatric profile such as MDD.

Placement and Confirmation of Stimulation Parameters Including Location.

In an embodiment, a method of determining a location for stimulation (i.e., a location of a magnetic field generator) includes the assessing step 94 with positioning of a first stimulator of at least first TMS device 104, stimulating, and determining if a desired change in an objective measure or in a reported symptom. The TMS device 104 is configured to provide stimulation using at least one coil or other magnetic field generator at a candidate location using at least a first stimulation signal having a selectable amplitude that is sufficient to evoke an evoked potential (EP) or motor evoked potential (MEP) response, or a change in cardiac activity such as HR or HRV. In an embodiment, an assessment procedure 94 includes positioning the stimulator at a candidate location and the stimulation is provided using a test stimulus to assess a stimulated related change occurs. If a response is not evoked then the stimulator position can be adjusted and the test signal again applied. The test stimulus can be different than (e.g., stronger, longer pulse duration) the treatment stimulus, and may be provided by a different device than is used during treatment.

For example, the test stimulus may be provided by a TMS device 104 that provides a stronger field to determine the appropriate location or other parameter to be used for stimulation. The treatment stimulus may then be provided by a stimulator of a second device 106 which is adjusted according to a candidate location that was found to be successful during the assessment procedure 94. In an embodiment, a patient/physician programmer 116 can transmit control signals to a TMS device 104 to cause it to provide a stimulation signal while also recording from a sensor of the stimulation/sensing module 112 in a time-locked manner to assess time-locked changes such as evoked brain or muscle activity.

System Architecture.

In an embodiment, the therapy device 104/106 is realized within in a single housing or alternatively may be at least partially distributed into electrically or wirelessly connected components each housed independently (and flexibly connected). The system 100 is provided with non-transitory computer-readable medium in the control subsystem 102, the devices 104/106, user device 114, and other system components that are configured for storing one or more sets of instructions configured to be executed as part of system operation. The system includes processors that can be at least one processor of control module of a stimulation device 104/106, a user device 114, and/or remote computers that communicate over the internet to cause the system to operate in a particular manner. It is understood that in different embodiments, selected system components are configured to provide the stimulation or participate in the therapy include related hardware such as a stimulus generator, TMS coils (and/or magnets), isolation circuitry, microprocessors, memory (e.g., RAM, ROM, flash memory, etc.), connectors, signal routing, batteries, power transformers, amplifiers, and hardware for providing communication and accepting user input. The components run upon software instructions and can operate using, for example and without limitation: firmware, operating systems, utilities, processes, algorithms, and methods/routines that allow the system to function. In an embodiment, when the instructions are executed by a processor of the stimulation device 104/106, the device executes a plurality steps comprising delivery of at least a first stimulation signal generated by the signal generator which is then used to drive an electrical, magnetic, or sonic stimulator.

Repetitive TMS can use electromagnets placed adjacent to the scalp that provides magnetic field pulses in the range of some MRI scans (e.g., a range of about 1.5-10 Tesla). Both rTMS and MRI devices may be configured to generate strong magnetic fields that can be greater than 10,000 Gauss (i.e. 1 Tesla). In embodiments, the invention includes lower-strength TMS devices and methods to provide a second type of TMS stimulation for modulating the electrical activity of a brain or spinal cord (or other body area) in a targeted manner using a magnetic field, such as in the range of 4,000 to 6,000 Gauss or a strength that is defined as subthreshold in that it is not sufficient to consistently evoke action potentials or is below a subjects MT. In embodiments, the type 2 TMS device can produce a magnetic field having a strength as low as about 50-60 Gauss.

In some embodiments, the magnetic field of the type 2 stimulation varies according to a waveform. In some embodiments, the waveform is a mono-phasic rectangular pulse, a bi-phasic rectangular pulse, a mono-phasic trapezoidal pulse, a bi-phasic trapezoidal pulse, a mono-phasic sinusoidal pulse, a bi-phasic sinusoidal pulse, a mono-phasic pulse train series, a bi-phasic pulse train series, or a sinusoid. In some embodiments, the waveform has a period of less than about 10 msec. In some embodiments, the waveform has a frequency between about 1 Hz and about 20 Hz.

In an embodiment, the subject is treated with type 2 TMS that provides <MT stimulation for an interval lasting from less than 1 minute up to about 2 hours. In an embodiment, the pulse of the type 2 TMS has a width of about 100 milliseconds, an amplitude of 3000 Gauss, a maximum rate of change in amplitude is about 227 Gauss/msec.

In an embodiment, the strength of an electric field induced in the cerebral cortex level by the TMS may be set at a strength that is modelled as being in the range of 0.02 V/m.

In an embodiment, the type 2 TMS uses oscillatory magnetic field stimuli which can be configured to produce stimulation using different sets of stimulation parameters related to stimulation frequencies and patterns. The characteristics of the different stimulation montages defined by the stimulation sets can be measured and calibrated for individual heads. For example, field strengths and directions of voltages induced in magnetic field sensors can be used to obtain energy measures oriented along all three orthogonal axes. These measurements can then be used to adjust the stimulation programs. The field strength may be further improved using diametrically magnetized magnets. Multiple magnetic stimulators (e.g., permanent magnets) can be operated in combination to create spatiotemporal stimulation patterns customized for each patient.

In an embodiment, type 2 TMS uses a device such as that described in U.S. Pat. No. 6,402,678, which is included herein by reference. The device produces a 0.9 tesla pulse at 1 cm from the device. In accordance with Clause 4.3 of IEC 60601-1, the Essential Performance of the TMS used in the home does not deliver a pulse above 0.95T. At treatment, 1 to 4 magnetic field pulses are delivered of nominally 0.9 T, measured 1 cm from the device surface, with a rise time of 180 μsec and a total pulse length of less than 1 ms. In embodiments, for the type 2 TMS therapy, the maximum pulse intensity at the center of the spherical cap coil is greater than 0.2 Tesla and the maximum pulse intensity is 1.0±0.5 Tesla. The pulse rise time is between approximately 100 and 300 milliseconds.

In embodiments, the waveform for treatment using Type 2 TMS would include delivery of a magnetic pulse with a rise time between 10 and 1,000 microseconds. A pulse length of about 200 microseconds may be selected. The stimulation pulse rate would optimally be at a rate between 0.1 Hz and 10 Hz with a frequency of about 0.5 to 1.0 Hz. The waveform could be approximately half of one sine wave or a square wave when providing the relief of pain. The peak amplitude for the magnetic pulses at the patient's skin may be set to between at least 0.1 Tesla and about 0.5 Tesla.

In an embodiment, the second TMS treatment protocol includes providing TMS treatment using a strength that is >MT when using longer pulse width, but is provided at a reduced frequency rate or with a very short pulse duration so that it is <MT. For example, while the first TMS protocol may set the rate to be equal to a subject's EEG frequency such as 9 or 10 Hz, the second rate may be only 1 Hz or less. The second rate can be as little as a few pulses per day.

This application contains section headings that are provided for organizational reasons only and are not meant to limit the invention in any manner.

References and citations to other documents, such as patents, patent applications, patent publications, journals, books, papers, have been made throughout this disclosure. All such documents are hereby incorporated herein by reference in their entirety for all purposes.

Disorders treated by magnetic or electrical stimulation include, for example, psychiatric disorders, migraine and headaches disorders, epileptic seizures, cardiac arrhythmias, and sleep disorders (e.g., insomnia) In some embodiments the invention can be used to improve a psychiatric disorder, or at least its symptoms, selected from the group consisting of depression, schizophrenia, bipolar, anxiety, obsessive-compulsive, movement disorders, Parkinson's disease, attention deficit hyperactivity disorder (ADHD), autism, substance abuse/drug addiction, head injury, eating disorder, tinnitus, or to improve symptoms of a disorders such as fibromyalgia. In embodiment the treatment may also be related to disorders, such as, traumatic brain injury, Alzheimer's Disease, coma, post-traumatic stress disorder (PTSD), and any combination thereof. In embodiments, the systems and methods can be used to treat cardiovascular disorders such as heart failure, high blood pressure, arrythmia, and/or to modulate heart rate variability.

Stimulation can be provided to improve a condition or process in the brain or body including increasing calm, improved cognitive processing, memory, reaction times, or promoting sleep, health or wellbeing. Treatment of disorders can include producing a desired improvement of any patient state or condition such as promotion of weight loss or decrement in appetite. Stimulation can be directed to central or peripheral nervous system targets and can be, for example, transcutaneous or transcranial stimulators, or can be provided by implanted stimulators.

EQUIVALENTS

The invention may be embodied in other specific forms without departing from the spirit or essential characteristics thereof. The foregoing embodiments are therefore to be considered in all respects illustrative rather than limiting on the invention described herein.

The various steps disclosed herein (such as, for non-limiting example, logic that performs a function or process) may be described as data and/or instructions embodied in various computer-readable media, in terms of their behavioral, and/or other characteristics. The logic and methods described herein may comprise, according to various embodiments of the invention, software, hardware, or a combination of software and hardware.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. When the word "or" is used about a list of two or more items, then that word covers the following interpretations of the word: any of the items, all of the items, and any combination of the items in the list.

The above descriptions of illustrated embodiments of the system, methods, or devices are not intended to be exhaustive or to be limited to the precise form disclosed. While specific embodiments of, and examples for, the system, methods, or devices are described herein for illustrative purposes, various equivalent modifications are possible within the scope of the system, methods, or devices, as those skilled in the relevant art will recognize. The teachings of the system, methods, or devices provided herein can be applied to other processing systems, methods, or devices, not only for the systems, methods, or devices described. Any system component or step of a method that has been disclosed can be omitted, practiced in isolation, or repeated without departing from the scope of the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention.

What is claimed is:

1. A method of providing a coordinated combination transcranial magnetic stimulation (TMS) treatment regimen to treat a disorder of a patient by stimulating a brain of the patient, comprising:

providing a first TMS treatment protocol during at least a first set of treatment sessions using a first TMS device that is a coil-based TMS device in a clinical setting that provides a first type of magnetic stimulation therapy to the brain in accordance with said first TMS treatment protocol by transmitting a first TMS signal having a first magnetic field strength that is set based upon a patient's motor threshold; and establishing a second TMS treatment protocol for providing a second type of magnetic stimulation therapy to the brain during at least a second set of treatment sessions using a second TMS device that uses at least one permanent magnet, said second TMS treatment protocol being used in a location that is not said clinical setting and that provides the second type of magnetic stimulation therapy by transmitting a second TMS signal having a second magnetic field strength;

wherein the second TMS device is configured such that the magnetic field strength of the second TMS signal is limited to be below the first magnetic field strength, and wherein the first and second treatment protocols are coordinated as parts of the coordinated combination TMS treatment regimen for the patient.

2. The method of claim 1, wherein the coordinated combination transcranial magnetic stimulation treatment regimen creates a combination of the first TMS treatment protocol and the second TMS treatment protocol, and wherein said combination transcranial magnetic stimulation treatment uses a combination transcranial magnetic stimulation treatment protocol with a treatment schedule and parameter values for the first and second TMS treatment protocols that are designed for a treatment for depression.

3. The method of claim 1, wherein the coordinated combination transcranial magnetic stimulation treatment regimen is only provided to the patient if the patient previously passed a screening assessment procedure demonstrating said patient's motor threshold was determined to be at or below a selected stimulation strength.

4. The method of claim 1, wherein the second type of magnetic stimulation therapy is a targeted stimulation of at least one cranial nerve, whereby a lower magnitude of stimulation is applied to at least one target that is closer to the at least one permanent magnet of the second TMS device than the patient's brain.

5. The method of claim 1, wherein the second TMS device does not require liquid cooling.

6. The method of claim 1, wherein the second TMS treatment protocol is defined based at least in part on one or more parameters of the first TMS treatment protocol, and a fixed positional location of the at least one permanent magnet of the second TMS device is maintained in the fixed positional location with respect to the patient's brain during the at least a second set of treatment sessions.

7. The method of claim 1, wherein the first TMS treatment protocol is an induction protocol and said induction protocol is followed by the second TMS treatment protocol that is a maintenance protocol.

8. The method of claim 1, wherein the first TMS treatment protocol includes said first set of treatment sessions and the second TMS treatment protocol is provided between at least two consecutive treatment sessions of the first set of treatment sessions wherein a minimum inter-session interval between consecutive stimulation sessions of the coordinated combination transcranial magnetic stimulation treatment regimen is less than an inter-session interval between the at least two consecutive treatment sessions of the first set of treatment sessions, thereby reinforcing the first type of magnetic stimulation therapy and producing an improvement in patient symptoms relative to providing only the first set of treatment sessions.

9. The method of claim 1, wherein the first type of magnetic stimulation therapy is provided during said first set of treatment sessions and the second type of magnetic stimulation therapy is provided between at least a portion of the first set of treatment sessions, whereby at least one inter-session interval between consecutive treatment sessions of the first set of treatment sessions is increased relative to a treatment schedule that does not include the second type of magnetic stimulation therapy thereby reducing a frequency of clinic visits required for the patient.

10. The method of claim 1, wherein the second TMS treatment protocol is configured to provide the second TMS signal and the second magnetic field strength is below a motor threshold for a reference group of patients.

11. The method of claim 1, wherein the second magnetic field strength is below the motor threshold for the patient.

12. The method of claim 1, wherein the second magnetic field strength is a magnetic field strength that meets a first treatment threshold and produces a change in a heart rate of the patient.

13. The method of claim 1, wherein the second magnetic field strength of the second TMS signal produces a change in an ocular measurement.

14. The method of claim 1, wherein the second magnetic field strength is also sufficient to produce a time-locked change in an optical measurement which is an near infrared spectroscopy (NIRS) measurement, said time locked change occurring over a definite period of time in response to provision of the second TMS signal.

15. The method of claim 1, wherein the second magnetic field strength also has a magnitude sufficient to produce a change in cardiac activity of the patient.

16. The method of claim 1, wherein the second magnetic field strength is a magnetic field strength that also produces a change in a measure sensed from the patient which is associated with parasympathetic nervous system arousal state.

17. The method of claim 1, wherein the second magnetic field strength is below 1 tesla.

18. The method of claim 1, wherein the second magnetic field strength is about 0.60 to 0.85 tesla.

19. The method of claim 1, wherein the first TMS treatment protocol includes a provision of transcranial magnetic stimulation that occurs at least five times a week during an induction interval and is followed by a provision of the second type of magnetic stimulation therapy according to the second TMS treatment protocol that includes transcranial magnetic stimulation that occurs at least every other day during a maintenance interval.

20. The method of claim 1, wherein the coordinated combination transcranial magnetic stimulation treatment regimen is defined by a protocol that combines the first TMS treatment protocol that includes a provision of transcranial magnetic stimulation treatment that occurs for the first set of treatment sessions using the first TMS device that is a coil-based TMS device and the second type of magnetic stimulation therapy that uses a set of rotating permanent magnets of the at least one permanent magnet to provide transcranial magnetic stimulation treatment during the at least one second set of treatment sessions.

21. The method of claim 1, wherein the first TMS treatment protocol of the first type of magnetic stimulation therapy uses stimulation parameter values defined for a first processor of the first TMS device defined to provide therapy and the second TMS treatment protocol of the second type of magnetic stimulation therapy has a second set of stimulation parameter values defined to provide therapy for a second processor in the second TMS device.

22. The method of claim 1, wherein the combination treatment regimen adjusts the second TMS treatment protocol of the second type of magnetic stimulation therapy having a second set of stimulation parameter values defined for a treatment series protocol, wherein said adjusting includes inter-session intervals between treatment sessions that is at least partially based upon a timing of the first set of treatment sessions of the first treatment protocol.

23. The method of claim 1, wherein a combination treatment protocol defines a schedule for the first TMS treatment protocol including inter-session interval parameters for the first set of treatment sessions based upon the second TMS treatment protocol and a schedule for the second set of treatment sessions.

* * * * *